(12) United States Patent
Lipkens et al.

(10) Patent No.: US 11,179,747 B2
(45) Date of Patent: *Nov. 23, 2021

(54) NON-PLANAR AND NON-SYMMETRICAL PIEZOELECTRIC CRYSTALS AND REFLECTORS

(71) Applicant: FloDesign Sonics, Inc., Wilbraham, MA (US)

(72) Inventors: Bart Lipkens, Hampden, MA (US); Walter M Presz, Jr., Wilbraham, MA (US); Kedar Chitale, West Hartford, CT (US); Thomas J Kennedy, III, Wilbraham, MA (US); Rudolf Gilmanshin, Framingham, MA (US); Dane Mealey, Springfield, MA (US); Brian Dutra, East Longmeadow, MA (US); David Sokolowski, Wilbraham, MA (US)

(73) Assignee: FloDesign Sonics, Inc., Wilbraham, MA (US)

(*) Notice: Subject to any disclaimer, the term of this patent is extended or adjusted under 35 U.S.C. 154(b) by 277 days.

This patent is subject to a terminal disclaimer.

(21) Appl. No.: 15/206,244

(22) Filed: Jul. 9, 2016

(65) Prior Publication Data

US 2017/0008029 A1 Jan. 12, 2017

Related U.S. Application Data

(60) Provisional application No. 62/190,715, filed on Jul. 9, 2015.

(51) Int. Cl.
*B06B 1/02* (2006.01)
*B01D 21/28* (2006.01)
(Continued)

(52) U.S. Cl.
CPC ........ *B06B 1/0238* (2013.01); *B01D 21/0009* (2013.01); *B01D 21/283* (2013.01);
(Continued)

(58) Field of Classification Search
CPC .................................................. B01B 1/0223
See application file for complete search history.

(56) References Cited

U.S. PATENT DOCUMENTS

| 2,473,971 A | 6/1949 | Ross |
| 2,667,944 A | 2/1954 | Crites |
| (Continued) | | |

FOREIGN PATENT DOCUMENTS

| CN | 102170949 A | 8/2011 |
| CN | 104363996 A | 2/2015 |
| (Continued) | | |

OTHER PUBLICATIONS

Alvarez et al.; Shock Waves, vol. 17, No. 6, pp. 441-447, 2008.
(Continued)

*Primary Examiner* — Rosanne Kosson
(74) *Attorney, Agent, or Firm* — FloDesign Sonics, Inc.

(57) ABSTRACT

An acoustophoretic device is disclosed. The acoustophoretic device includes an acoustic chamber, an ultrasonic transducer, and a reflector. The ultrasonic transducer includes a piezoelectric material driven by a voltage signal to create a multi-dimensional acoustic standing wave in the acoustic chamber emanating from a non-planar face of the piezoelectric material. A method for separating a second fluid or a particulate from a host fluid is also disclosed. The method includes flowing the mixture through an acoustophoretic device. A voltage signal is sent to drive the ultrasonic transducer to create the multi-dimensional acoustic standing wave in the acoustic chamber such that the second fluid or particulate is continuously trapped in the standing wave, and
(Continued)

then agglomerates, aggregates, clumps, or coalesces together, and subsequently rises or settles out of the host fluid due to buoyancy or gravity forces, and exits the acoustic chamber.

25 Claims, 23 Drawing Sheets

(51) Int. Cl.
  *B06B 1/06*     (2006.01)
  *B01D 21/00*    (2006.01)
  *B06B 3/04*     (2006.01)
  *C12M 1/00*    (2006.01)
  *H03H 9/17*     (2006.01)

(52) U.S. Cl.
  CPC .............. *B06B 1/0644* (2013.01); *B06B 3/04* (2013.01); *C12M 47/02* (2013.01); *H03H 9/17* (2013.01)

(56) References Cited

U.S. PATENT DOCUMENTS

| | | |
|---|---|---|
| 3,372,370 A | 3/1968 | Cyr |
| 3,555,311 A | 1/1971 | Weber |
| 4,055,491 A | 10/1977 | Porath-Furedi |
| 4,065,875 A | 1/1978 | Srna |
| 4,118,649 A | 10/1978 | Schwartzman et al. |
| 4,158,629 A | 6/1979 | Sawyer |
| 4,165,273 A | 8/1979 | Azarov et al. |
| 4,173,725 A | 11/1979 | Asai et al. |
| 4,204,096 A | 5/1980 | Barcus et al. |
| 4,254,661 A | 3/1981 | Kossoff et al. |
| 4,320,659 A | 3/1982 | Lynnworth et al. |
| 4,344,448 A | 8/1982 | Potts |
| 4,398,325 A | 8/1983 | Piaget et al. |
| 4,552,669 A | 11/1985 | Sekellick |
| 4,666,595 A | 5/1987 | Graham |
| 4,699,588 A | 10/1987 | Zinn et al. |
| 4,743,361 A | 5/1988 | Schram |
| 4,759,775 A | 7/1988 | Peterson et al. |
| 4,800,316 A | 1/1989 | Wang |
| 4,821,838 A | 4/1989 | Chen |
| 4,836,684 A | 6/1989 | Javorik et al. |
| 4,878,210 A | 10/1989 | Mitome |
| 4,983,189 A | 1/1991 | Peterson et al. |
| 5,062,965 A | 11/1991 | Bernou et al. |
| 5,085,783 A | 2/1992 | Feke et al. |
| 5,164,094 A | 11/1992 | Stuckart |
| 5,225,089 A | 7/1993 | Benes et al. |
| 5,371,729 A | 12/1994 | Manna |
| 5,395,592 A | 3/1995 | Bolleman et al. |
| 5,431,817 A | 7/1995 | Braatz et al. |
| 5,443,985 A | 8/1995 | Lu et al. |
| 5,452,267 A | 9/1995 | Spevak |
| 5,484,537 A | 1/1996 | Whitworth |
| 5,527,460 A | 6/1996 | Trampier et al. |
| 5,560,362 A | 10/1996 | Sliwa, Jr. et al. |
| 5,594,165 A | 1/1997 | Madanshetty |
| 5,604,301 A | 2/1997 | Mountford et al. |
| 5,626,767 A | 5/1997 | Trampier et al. |
| 5,688,405 A | 11/1997 | Dickinson et al. |
| 5,711,888 A | 1/1998 | Trampler et al. |
| 5,831,166 A | 11/1998 | Kozuka et al. |
| 5,834,871 A | 11/1998 | Puskas |
| 5,902,489 A | 5/1999 | Yasuda et al. |
| 5,912,182 A | 6/1999 | Coakley et al. |
| 5,947,299 A | 9/1999 | Vazquez et al. |
| 5,951,456 A | 9/1999 | Scott |
| 6,090,295 A | 6/2000 | Raghavarao et al. |
| 6,166,231 A | 12/2000 | Hoeksema |
| 6,216,538 B1 | 4/2001 | Yasuda et al. |
| 6,205,848 B1 | 6/2001 | Faber et al. |
| 6,273,262 B1 | 8/2001 | Yasuda et al. |
| 6,332,541 B1 | 12/2001 | Coakley et al. |
| 6,391,653 B1 | 5/2002 | Letcher et al. |
| 6,475,151 B2 | 11/2002 | Koger et al. |
| 6,482,327 B1 | 11/2002 | Mori et al. |
| 6,487,095 B1 | 11/2002 | Malik et al. |
| 6,592,821 B1 | 7/2003 | Wada et al. |
| 6,641,708 B1 | 11/2003 | Becker et al. |
| 6,649,069 B2 | 11/2003 | DeAngelis |
| 6,699,711 B1 | 3/2004 | Hahn et al. |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,008,540 B1 | 3/2006 | Weavers et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,322,431 B2 | 1/2008 | Ratcliff |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,837,040 B2 | 11/2010 | Ward et al. |
| 7,846,382 B2 | 12/2010 | Strand et al. |
| 7,968,049 B2 | 6/2011 | Takahashi et al. |
| 8,080,202 B2 | 12/2011 | Takahashi et al. |
| 8,134,705 B2 | 3/2012 | Kaduchak et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,592,204 B2 | 11/2013 | Lipkens et al. |
| 8,679,338 B2 | 3/2014 | Rietman et al. |
| 8,691,145 B2 | 4/2014 | Dionne et al. |
| 8,873,051 B2 | 10/2014 | Kaduchak et al. |
| 8,889,388 B2 | 11/2014 | Wang et al. |
| 9,272,234 B2 | 3/2016 | Lipkens et al. |
| 2002/0038662 A1 | 4/2002 | Schuler et al. |
| 2002/0134734 A1 | 9/2002 | Campbell et al. |
| 2003/0015035 A1 | 1/2003 | Kaduchak et al. |
| 2003/0028108 A1 | 2/2003 | Miller et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2004/0035208 A1 | 2/2004 | Diaz et al. |
| 2004/0112841 A1 | 6/2004 | Scott |
| 2004/0124155 A1 | 7/2004 | Meegan, Jr. |
| 2004/0149039 A1 | 8/2004 | Cardelius |
| 2005/0031499 A1 | 2/2005 | Meier |
| 2005/0121269 A1 | 6/2005 | Namduri |
| 2005/0145567 A1 | 7/2005 | Quintel et al. |
| 2005/0196725 A1 | 9/2005 | Fu |
| 2006/0037915 A1 | 2/2006 | Strand et al. |
| 2006/0037916 A1 | 2/2006 | Trampier |
| 2006/0050615 A1 | 3/2006 | Swisher |
| 2007/0053795 A1 | 3/2007 | Laugharn, Jr. et al. |
| 2007/0224676 A1 | 9/2007 | Haq |
| 2007/0267351 A1 | 11/2007 | Roach et al. |
| 2007/0272618 A1 | 11/2007 | Gou et al. |
| 2007/0284299 A1 | 12/2007 | Xu et al. |
| 2008/0011693 A1 | 1/2008 | Li et al. |
| 2008/0105625 A1 | 5/2008 | Rosenberg et al. |
| 2008/0217259 A1 | 9/2008 | Siversson |
| 2008/0245709 A1 | 10/2008 | Kaduchak et al. |
| 2008/0264716 A1 | 10/2008 | Kuiper et al. |
| 2008/0272034 A1 | 11/2008 | Ferren et al. |
| 2008/0272065 A1 | 11/2008 | Johnson |

(56) References Cited

U.S. PATENT DOCUMENTS

| | | |
|---|---|---|
| 2008/0316866 A1 | 12/2008 | Goodemote et al. |
| 2009/0029870 A1 | 1/2009 | Ward et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0126481 A1 | 5/2009 | Burris |
| 2009/0178716 A1 | 7/2009 | Kaduchak et al. |
| 2009/0194420 A1 | 8/2009 | Mariella, Jr. et al. |
| 2009/0253271 A1 | 10/2009 | Sinha et al. |
| 2009/0045107 A1 | 12/2009 | Ward et al. |
| 2009/0295505 A1 | 12/2009 | Mohammadi et al. |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1 | 5/2011 | Dionne et al. |
| 2011/0125024 A1 | 5/2011 | Mueller |
| 2011/0146678 A1 | 6/2011 | Ruecroft et al. |
| 2011/0154890 A1 | 6/2011 | Holm et al. |
| 2011/0166551 A1 | 7/2011 | Schafer |
| 2011/0189732 A1 | 8/2011 | Weinand et al. |
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0163126 A1 | 6/2012 | Campbell et al. |
| 2012/0175012 A1 | 7/2012 | Goodwin et al. |
| 2012/0267288 A1 | 10/2012 | Chen et al. |
| 2012/0325727 A1 | 12/2012 | Dionne et al. |
| 2012/0325747 A1 | 12/2012 | Reitman et al. |
| 2012/0328477 A1 | 12/2012 | Dionne et al. |
| 2012/0329122 A1 | 12/2012 | Lipkens et al. |
| 2013/0115664 A1 | 5/2013 | Khanna et al. |
| 2013/0175226 A1 | 7/2013 | Coussios et al. |
| 2013/0217113 A1 | 8/2013 | Srinivasan et al. |
| 2013/0277316 A1 | 10/2013 | Dutra et al. |
| 2013/0277317 A1 | 10/2013 | LoRicco et al. |
| 2013/0284271 A1 | 10/2013 | Lipkens et al. |
| 2014/0011240 A1 | 1/2014 | Lipkens et al. |
| 2014/0017758 A1 | 1/2014 | Kniep et al. |
| 2014/0102947 A1 | 4/2014 | Baym et al. |
| 2014/0141413 A1 | 5/2014 | Laugham, Jr. et al. |
| 2014/0204717 A1 | 7/2014 | Kunkel et al. |
| 2014/0319077 A1 | 10/2014 | Lipkens et al. |
| 2014/0377834 A1 | 12/2014 | Presz, Jr. et al. |

FOREIGN PATENT DOCUMENTS

| | | | |
|---|---|---|---|
| DE | 30 27 433 A1 | 2/1982 | |
| DE | 32 18 488 A1 | 11/1983 | |
| DE | 196 48 519 A1 | 6/1998 | |
| DE | 10 2008 006 501 A1 | 9/2008 | |
| EP | 0 292 470 B1 | 11/1988 | |
| EP | 0 641 606 | 3/1995 | |
| EP | 1 254 669 B1 | 11/2002 | |
| GB | 2 420 510 A | 5/2006 | |
| JP | 9-136090 | 5/1997 | |
| WO | WO 1987/07178 A1 | 12/1987 | |
| WO | WO 90/05008 | 3/1990 | |
| WO | WO 1998/017373 | 4/1998 | |
| WO | WO 98/50133 A1 | 11/1998 | |
| WO | WO 02/072234 A1 | 9/2002 | |
| WO | WO 2004/079716 A1 | 9/2004 | |
| WO | WO 2009/111276 A1 | 9/2009 | |
| WO | WO 2009/144709 A1 | 12/2009 | |
| WO | WO 2010/024753 A1 | 4/2010 | |
| WO | WO 2010/040394 A1 | 4/2010 | |
| WO | WO 2011/023949 A2 | 3/2011 | |
| WO | WO 2011/025890 A1 | 3/2011 | |
| WO | WO 2011/027146 A2 | 3/2011 | |
| WO | WO 2011/131947 A2 | 10/2011 | |
| WO | WO 2011/161463 A2 | 12/2011 | |
| WO | WO 2013/043297 A1 | 3/2013 | |
| WO | WO 2013/055517 A1 | 4/2013 | |
| WO | WO-2013049623 A1 * | 4/2013 | .......... A61M 5/1407 |
| WO | WO 2014/014941 A1 | 1/2014 | |
| WO | WO 2014/029505 A1 | 2/2014 | |
| WO | WO 2014/055219 A2 | 4/2014 | |
| WO | WO 2014/124306 A1 | 8/2014 | |
| WO | WO 2015/006730 A1 | 1/2015 | |

OTHER PUBLICATIONS

Benes et al.; Ultrasonic Separation of Suspended Particles, 2001 IEEE Ultrasonics Symposium; Oct. 7-10, 2001; pp. 649-659; Atlanta, Georgia.

Castro; Tunable gap and quantum quench dynamics in bilayer graphene; Jul. 13, 2010; Mathematica Summer School.

Cravotto et al.; Ultrasonics Sonochemistry, vol. 15, No. 5, pp. 898-902, 2008.

Garcia-Lopez, et al; Enhanced Acoustic Separation of Oil-Water Emulsion in Resonant Cavities. The Open Acoustics Journal. 2008, vol. 1, pp. 66-71.

Hill et al.; Ultrasonic Particle Manipulation; Microfluidic Technologies for Miniaturized Analysis Systems, Jan. 2007, pp. 359-378.

Ilinskii et al.; Acoustic Radiation Force on a Sphere in Tissue; AIP Conference Proceedings; 2012.

Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.

Latt et al.; Ultrasound-membrane hybrid processes for enhancement of filtration properties; Ultrasonics sonochemistry 13.4 (2006): 321-328.

Lipkens et al.; Frequency sweeping and fluid flow effects on particle trajectories in ultrasonic standing waves; Acoustics 08, Paris, Jun. 29-Jul. 4, 2008.

Lipkens et al.; Prediction and measurement of particle velocities in ultrasonic standing waves; J. Acoust. Soc. Am., 124 No. 4, pp. 2492 (A) 2008.

Lipkens et al.; Separation of micron-sized particles in macro-scale cavities by ultrasonic standing waves; Presented at the International Congress on Ultrasonics, Santiago; Jan. 11-17, 2009.

Lipkens et al.; The effect of frequency sweeping and fluid flow on particle trajectories in ultrasonic standing waves; IEEE Sensors Journal, vol. 8, No. 6, pp. 667-677, 2008.

Lipkens et al.; Separation of bacterial spores from flowering water in macro-scale cavities by ultrasonic standing waves; submitted/uploaded to arxiv.org/abs/1006.5467 on Jun. 28, 2010.

Lipkens et al., Macro-scale acoustophoretic separation of lipid particles from red blood cells, The Journal of the Acoustical Society of America, vol. 133, Jun. 2, 2013, p. 045017, XP055162509, New York, NY.

Meribout et a.; An Industrial-Prototype Acoustic Array for Real-Time Emulsion Layer Detection in Oil Storage Tanks; IEEE Sensors Journal, vol. 9, No. 12, Dec. 2009.

Nilsson et al.; Review of cell and particle trapping in microfluidic systems; Department of Measurement Technology and Industrial Electrical Engineering, Div. of Nanobiotechnology, Lund University, p.O. Box 118. Lund, Sweden, Analytica Chimica Acta 649, Jul. 14, 2009, pp. 141-157.

(56) References Cited

OTHER PUBLICATIONS

Pangu et al.; Droplet transport and coalescence kinetics in emulsions subjected to acoustic fields; Ultrasonics 46, pp. 289-302 (2007).
Ponomarenko et al.; Density of states and zero Landau level probed through capacitance of graphene; Nature Nanotechnology Letters, Jul. 5, 2009; Doi: 10.1038/NNANO.2009.177.
Seymour et al., J. Chern. Edu., 1990, 67(9), p. 763, published Sep. 1990.
Volpin et al.; Mesh simplification with smooth surface reconstruction; Computer-Aided Design; vol. 30; No. 11; 1998.
Wang et al.; Retention and Viability Characteristics of Mammalian Cells in an Acoustically Driven Polymer Mesh; Biotechnol. Prog. 2004, pp. 384-387 (2004).
Annex to Form PCT/ISA/206—Communication Relating to the Results of the Partial International Search Report, dated Jul. 18, 2013.
European Search Report of European Application No. 11769474.5, dated Sep. 5, 2013.
European Search Report of European Application No. 13760840.2, dated Feb. 4, 2016.
International Search Report and Written Opinion dated Dec. 20, 2011, for corresponding PCT application No. PCT/US2011/032181.
International Search Report and Written Opinion dated Feb. 27, 2012, for PCT application No. PCT/US2011/040787.
International Search Report and Written Opinion of International Application No. PCT/US2012/051804 dated Nov. 16, 2012.
International Search Report and Written Opinion of International Application No. PCT/US2013/037404 dated Jun. 21, 2013.
International Search Report and Writte PCT/US2013/032705 dated Jul. 26, 2013.
International Search Report and Writte PCT/US2013/050729 dated Sep. 25, 2013.
International Search Report dated Feb. 18, 2014 in corresponding PCT Application No. PCT/US2013/059640.
International Search Report for corresponding PCT Application Serial No. PCT/US2014/015382 dated May 6, 2014.
International Search Report for PCT/US2014/035557 dated Aug. 27, 2014.
International Search Report for PCT/US2014/043930 dated Oct. 22, 2014.
International Search Report for PCT/US2014/046412 dated Oct. 27, 2014.
International Search Report for PCT/US2014/064088 dated Jan. 30, 2015.
Extended European Search Report for Application No. EP 12833859.7 dated Mar. 20, 2015.
International Search Report and Written Opinion for International Application No. PCT/US2015/010595 dated Apr. 15, 2015.
International Search Report for PCT/US2015/019755 dated May 4, 2015.
International Search Report dated Jul. 30, 2015 for International Application No. PCT/US2015/030009.
International Search Report for PCT/US2015/039125 dated Sep. 30, 2015.
International Search Report and Written Opinion for PCT Application Serial No. PCT/US2015/053200 dated Dec. 28, 2015.
European Search Report of European Application No. 11796470.0 dated Jan. 5, 2016.
International Search Report and Written Opinion for International Application No. PCT/US2015/066884, dated Mar. 22, 2016.
International Search Report and Written Opinion for International Application No. PCT/US2016/024082 dated Jun. 27, 2016.
International Search Report and Written Opinion for International Application No. PCT/US2016/031357 dated Jul. 26, 2016.
International Search Report and Written Opinion for International Application No. PCT/US2016/041664 dated Oct. 18, 2016.
phys. org. "Engineers develop revolutionary nanotech water desalination membrane." Nov. 6, 2006. phys.org/news82047372.html.
"Proceedings of the Acoustics 2012 Nantes Conference," Apr. 23-27, 2012, Nantes, France, pp. 278-282.
Sony New Release: <www.sony.net/SonyInfo/News/Press/201010/10-137E/index.html>.

* cited by examiner

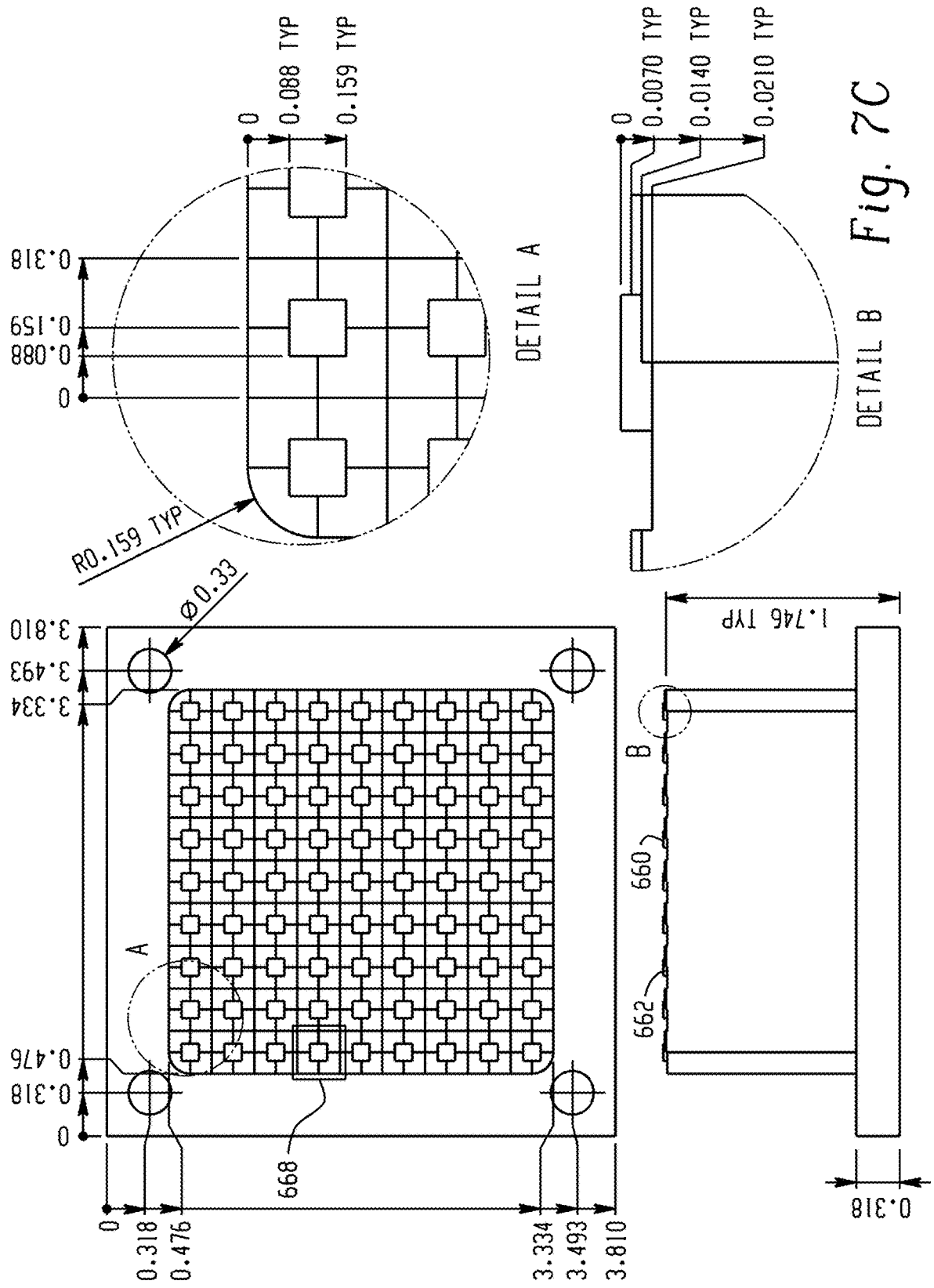

NON-PLANAR AND NON-SYMMETRICAL PIEZOELECTRIC CRYSTALS AND REFLECTORS

CROSS-REFERENCE TO RELATED APPLICATIONS

This application claims priority to U.S. Provisional Patent Application Ser. No. 62/190,715, filed on Jul. 9, 2015, the disclosure of which is hereby fully incorporated by reference in its entirety.

BACKGROUND

The present disclosure relates to the use of ultrasonically generated acoustic standing waves to achieve trapping, concentration, and separation of suspended-phase components and thereby remove such contaminants from a fluid medium such as water. The acoustic standing waves may be created by exciting the piezoelectric crystal of an ultrasonic transducer.

Piezoelectric crystals may be composed of any material that is able to generate a piezoelectric effect, i.e. vibrate when subjected to an external voltage. A conventional material that is used to make piezoelectric crystals is lead zirconate titanate (PZT). Piezoelectric ceramics are traditionally a mass of perovskite ceramic crystals composed of a small, tetravalent metal ion (e.g., titanium, zirconium) in a lattice of larger, divalent metal ions (e.g., lead, barium) and oxygen ions.

A piezoelectric PZT crystal can be made by mixing fine powders of the component metal oxides in specific proportions. This mixture is then heated to form a uniform powder. An organic binder is mixed with the metal oxides and formed into desired shapes (e.g., plates, rods, discs). The formed materials are heated at high temperatures that sinter the mixture and form a dense crystalline structure. The sintered parts are then cooled and subsequently shaped or trimmed to desired specifications. Electrodes are applied to the appropriate surfaces of the PZT crystal using processes such as electroless nickel plating or a silver/glass bead mixture coating that is heated and fused on the surface of the crystal.

Exposing the piezoelectric crystal to an electric charge (i.e. voltage) either in air or a liquid fluid generates pressure waves. A function generator may be used to apply a specific frequency or group of frequencies to the piezoelectric crystal such that the pressure waves have a specific frequency. An amplifier may be used to apply higher voltages to the piezoelectric crystal at the frequencies generated by the function generator. Conventionally, the face of the piezoelectric crystal is flat and thus the waves generated from the piezoelectric crystal are uniform across the face of the crystal.

A flat-faced piezoelectric crystal can be perturbed in a multi-mode fashion so as to generate multi-dimensional acoustic standing waves. These higher order modes of the piezoelectric crystal allow for multiple trapping lines to be formed in the acoustic standing wave, thus forming a multi-dimensional acoustic standing wave.

It would be desirable to provide a piezoelectric crystal that can be perturbed by a single excitation, yet still generate a multi-dimensional acoustic standing wave(s).

BRIEF DESCRIPTION

The present disclosure relates, in various embodiments, to acoustophoretic devices and methods of separating a second fluid or a particulate from a host fluid. Briefly, a multi-dimensional acoustic standing wave(s) emanating from a non-planar face of a piezoelectric material is used to continuously trap the second fluid or particulate, which then agglomerates, aggregates, clumps, or coalesces together, and subsequently rises or settles out of the host fluid due to buoyancy or gravity forces, and exits the acoustic chamber. The non-planar piezoelectric material only needs to be exposed to a single frequency, rather than a group of frequencies, to generate a multi-dimensional acoustic standing wave.

Disclosed in various embodiments herein are acoustophoretic devices, comprising: an acoustic chamber having at least one inlet and at least one outlet; at least one ultrasonic transducer located on a wall of the acoustic chamber; and a reflector located on a wall on the opposite side of the acoustic chamber from the at least one ultrasonic transducer. The at least one ultrasonic transducer includes a piezoelectric material driven by a voltage signal to create a multi-dimensional acoustic standing wave in the acoustic chamber emanating from a non-planar face of the piezoelectric material.

In certain embodiments, the non-planar face of the piezoelectric material is poled in a direction substantially perpendicular to a second face of the piezoelectric material. The non-planar face of the piezoelectric material can be defined by a step function or a smooth function.

In certain embodiments, the reflector also has a non-planar surface, which can be defined by a step function or a smooth function.

In certain embodiments, the piezoelectric material may be planar and the reflector will have a non-planar surface.

The at least one ultrasonic transducer can have a non-symmetrical shape, such as a trapezoidal shape. The reflector can also have a non-symmetrical shape, such as a trapezoidal shape.

Also disclosed herein are methods for separating a second fluid or a particulate from a host fluid. The methods comprise flowing a mixture of the host fluid and the second fluid or particulate through an acoustophoretic device. The acoustophoretic device comprises an acoustic chamber having at least one inlet and at least one outlet; at least one ultrasonic transducer located on a wall of the acoustic chamber; and a reflector located on a wall on the opposite side of the acoustic chamber from the at least one ultrasonic transducer. The at least one ultrasonic transducer includes a piezoelectric material driven by a voltage signal to create a multi-dimensional acoustic standing wave in the acoustic chamber emanating from a non-planar face of the piezoelectric material. The methods further comprise sending a voltage signal to drive the at least one ultrasonic transducer to create the multi-dimensional acoustic standing wave in the acoustic chamber such that the second fluid or particulate is continuously trapped in the standing wave, and then agglomerates, aggregates, clumps, or coalesces together, and continuously rises or settles out of the host fluid due to enhanced buoyancy or gravity forces, and exits the acoustic chamber.

The voltage signal can be a sinusoidal, triangular, pulsed or similar waveform. The voltage signal can have a frequency of from about 100 kHz to about 20 MHz.

In certain embodiments, the mixture of the host fluid and the second fluid or particulate is continuously flowed through the acoustic chamber. The second fluid or particulate can include at least one cell selected from the group consisting of CHO cells, T-cells, and yeast cells. Flow rates through the acoustic chamber can be from about 1 mL per minute to about 50 liters per hour. The methods and devices of the present disclosure may be capable of separation efficiencies of 90% and more for cell concentrations from as low as 50,000 cells per milliliter of fluid to 80,000,000 cells per milliliter of fluid.

Separation of materials may also include particulates separated from a primary fluid. This would include microspheres, microbubbles, microcarriers and the like. These materials may be solid or hollow and have a positive or negative contrast factor.

Also in various embodiments herein are acoustophoretic devices, comprising: an acoustic chamber having at least one inlet and at least one outlet; at least one ultrasonic transducer located on a wall of the acoustic chamber; and a reflector located on a wall on the opposite side of the acoustic chamber from the at least one ultrasonic transducer. The at least one ultrasonic transducer includes a piezoelectric material driven by a voltage signal to create a multi-dimensional acoustic standing wave in the acoustic chamber emanating from a first face of the piezoelectric material, and the reflector includes a faceted surface. The first face of the ultrasonic transducer can be planar. The faceted surface of the reflector can include a plurality of facet clusters or a plurality of wells.

In particular embodiments, the multi-dimensional standing wave results in an acoustic radiation force having an axial force component and a lateral force component that are the same order of magnitude. In particular embodiments, the acoustic standing wave may be a multi-dimensional acoustic standing wave (e.g., a three-dimensional acoustic standing wave). Examples of such multi-dimensional acoustic standing waves can be found in commonly owned U.S. Pat. No. 9,228,183, the entire contents of which are hereby fully incorporated by reference. In other embodiments, the acoustic standing wave can be a planar acoustic standing wave. Further yet, in particular embodiments, the acoustic standing wave may be a combination of a planar acoustic standing wave and a multi-dimensional acoustic standing wave, such as where the planar acoustic standing wave and multidimensional acoustic standing wave are super-positioned on each other.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 7C illustrates a third exemplary configuration of the faceted surface of the reflector of FIG. 6.

In FIG. 14A, the excitation pattern is generated at a frequency of 2.217 MHz. The right-hand scale is in units of $10^{-9}$, and ranges from 0.55 to 1 in intervals of 0.05. The maximum value is $2.25 \times 10^{-9}$, and the minimum value is $2.18 \times 10^{-11}$.

In FIG. 14B, the excitation pattern is generated at a frequency of 2.302 MHz. The right-hand scale is in units of $10^{-10}$, and ranges from 3 to 6 in intervals of 0.5. The maximum value is $1.38 \times 10^{-9}$, and the minimum value is $1.64 \times 10^{-11}$.

In FIG. 14C, the excitation pattern is generated at a frequency of 2.32 MHz. The right-hand scale is in units of $10^{-10}$, and ranges from 2.5 to 6 in intervals of 0.5. The maximum value is $1.11 \times 10^{-9}$, and the minimum value is $1.4 \times 10^{-11}$.

In FIG. 14D, the excitation pattern is generated at a frequency of 2.34 MHz. The right-hand scale is in units of $10^{-10}$, and ranges from 3 to 5 in intervals of 0.5. The maximum value is $9.23 \times 10^{-10}$, and the minimum value is $8.98 \times 10^{-12}$.

DETAILED DESCRIPTION

Figure 1:
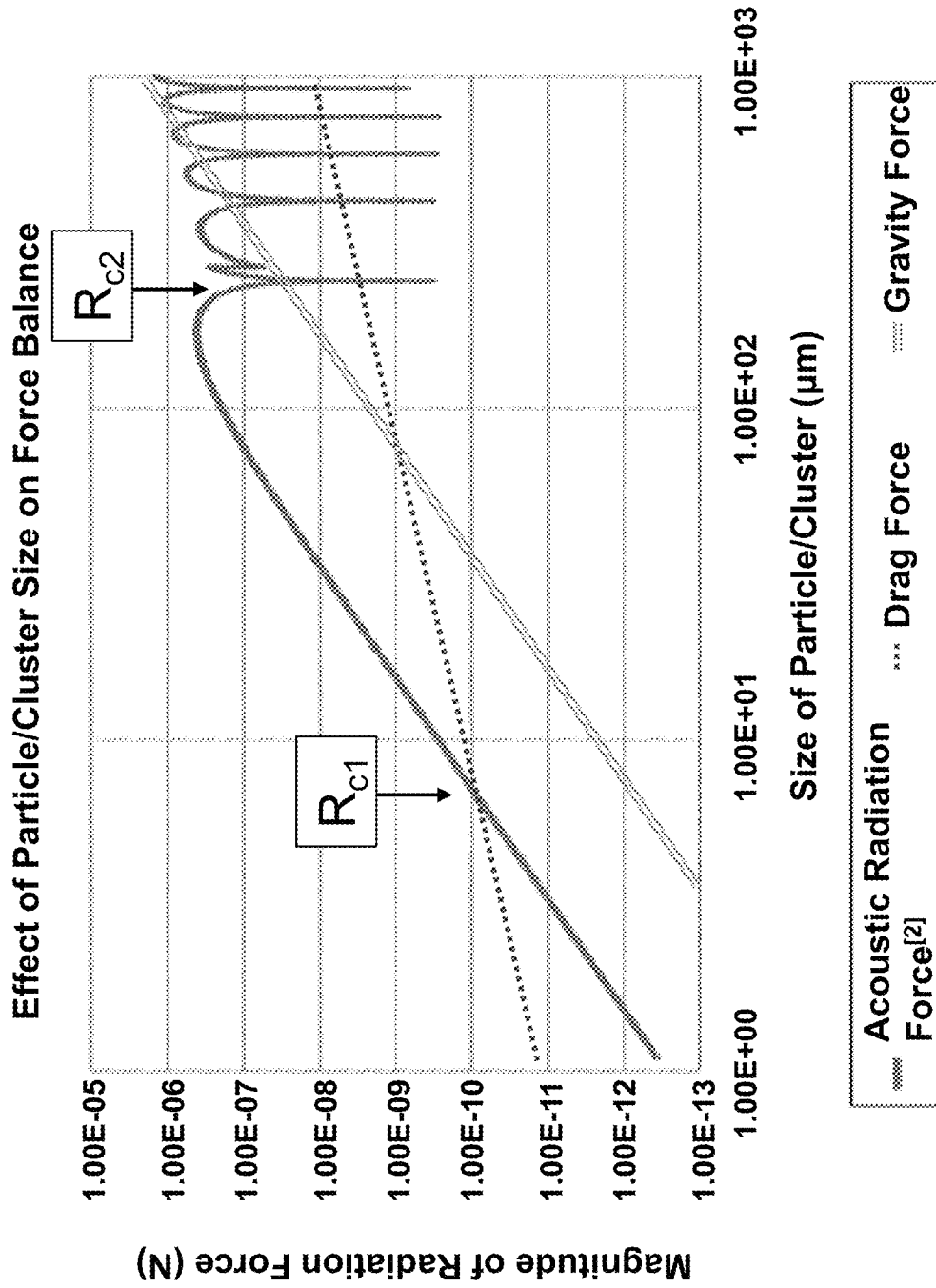
FIG. 1 is a graph showing the relationship of the acoustic radiation force, gravity/buoyancy force, and Stokes' drag force to particle size. The horizontal axis is in microns (μm) and the vertical axis is in Newtons (N).

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as requiring the presence of the named component and allowing the presence of other components. The term "comprising" should be construed to include the term "consisting of", which allows the presence of only the named component, along with any impurities that might result from the manufacture of the named component.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" used in connection with a quantity is inclusive of the stated value and has the meaning dictated by the context. When used in the context of a range, the modifier "about" should also be considered as disclosing the range defined by the absolute values of the two endpoints. For example, the range of "from about 2 to about 10" also discloses the range "from 2 to 10." The term "about" may refer to plus or minus 10% of the indicated number. For example, "about 10%" may indicate a range of 9% to 11%, and "about 1" may mean from 0.9-1.1.

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" or "base" are used to refer to surfaces where the top is always higher than the bottom/base relative to an absolute reference, i.e. the surface of the earth. The terms "upwards" and "downwards" are also relative to an absolute reference; upwards is always against the gravity of the earth.

The term "parallel" should be construed in its lay sense of two surfaces that maintain a generally constant distance between them, and not in the strict mathematical sense that such surfaces will never intersect when extended to infinity.

The present application refers to "the same order of magnitude." Two numbers are of the same order of magnitude if the quotient of the larger number divided by the smaller number is a value of at least 1 and less than 10.

Acoustophoresis is the separation of particles and secondary fluids from a primary or host fluid using high-intensity acoustic standing waves, and without the use of membranes or physical size exclusion filters. It has been known that high intensity standing waves of sound can exert forces on particles in a fluid when there is a differential in both density and/or compressibility, otherwise known as the acoustic contrast factor. The pressure profile in a standing wave contains areas of local minimum pressure amplitudes at its nodes and local maxima at its anti-nodes. Depending on the density and compressibility of the particles, they will be trapped at the nodes or anti-nodes of the standing wave. Generally, the higher the frequency of the standing wave, the smaller the particles that can be trapped due the pressure of the standing wave.

When acoustic standing waves propagate in liquids, the fast oscillations may generate a non-oscillating force on particles suspended in the liquid or on an interface between liquids. This force is known as the acoustic radiation force. The force originates from the non-linearity of the propagating wave. As a result of the non-linearity, the wave is distorted as it propagates and the time-averages are nonzero. By serial expansion (according to perturbation theory), the first non-zero term will be the second-order term, which accounts for the acoustic radiation force. The acoustic radiation force on a particle, or a cell, in a fluid suspension is a function of the difference in radiation pressure on either side of the particle or cell. The physical description of the radiation force is a superposition of the incident wave and a scattered wave, in addition to the effect of the non-rigid particle oscillating with a different speed compared to the surrounding medium thereby radiating a wave. The following equation presents an analytical expression for the acoustic radiation force on a particle, or cell, in a fluid suspension in a planar standing wave.

$$F_R = \frac{3\pi P_0^2 V_P \beta_m}{2\lambda} \varphi(\beta, \rho) \sin(2kx) \quad (1)$$

where $\beta_m$ is the compressibility of the fluid medium, $\rho$ is density, $\varphi$ is acoustic contrast factor, $V_p$ is particle volume, $\lambda$ is wavelength, k is $2\pi/\lambda$, $P_0$ is acoustic pressure amplitude, x is the axial distance along the standing wave (i.e., perpendicular to the wave front), and $$\varphi(\beta, \rho) = \frac{5\rho_p - 2\rho_m}{2\rho_p + \rho_m} - \frac{\beta_p}{\beta_m}$$

where $\rho_p$ is the particle density, $\rho_m$ is the fluid medium density, $\beta_p$ is the compressibility of the particle, and $\beta_m$ is the compressibility of the fluid medium.

In a typical experiment, the system is operated at a voltage such that the particles are trapped in the ultrasonic standing wave, i.e., remain in a stationary position. The axial component of the acoustic radiation force drives the particles, with a positive contrast factor, to the pressure nodal planes, whereas particles with a negative contrast factor are driven to the pressure anti-nodal planes. The radial or lateral component of the acoustic radiation force is the force that traps the particle. It therefore must be larger than the combined effect of fluid drag force and gravitational force. For small particles or emulsions, the drag force $F_D$ can be expressed as:

$$\vec{F}_D = 4\pi\mu_f R_P (\vec{U}_f - \vec{U}_p) \left[ \frac{1 + \frac{3}{2}\hat{\mu}}{1 + \hat{\mu}} \right] \quad (1)$$

where $U_f$ and $U_p$ are the fluid and particle velocity, $R_p$ is the particle radius, $\mu_f$ and $\mu_p$ are the dynamic viscosity of the fluid and particle, and $\hat{\mu}=\mu_p/\mu_f$ is the ratio of dynamic viscosities. The buoyancy force $F_B$ is expressed as:

$$F_B = \tfrac{4}{3}\pi R_p^3 (\rho_f - \rho_p) g \quad (2)$$

where $R_p$ is the particle radius, $\rho_f$ is the fluid density, $\rho_p$ is the particle density, and g is the universal gravitational constant.

For a particle to be trapped in the ultrasonic standing wave, the force balance on the particle must be zero, and therefore an expression for lateral acoustic radiation force $F_{LRF}$ can be found, which is given by:

$$F_{LRF} = F_D + F_B \quad (3)$$

For a particle of known size and material property, and for a given flow rate, this equation can be used to estimate the magnitude of the lateral acoustic radiation force.

The theoretical model that is used to calculate the acoustic radiation force is the formulation developed by Gor'kov, where the primary acoustic radiation force $F_R$ is defined as a function of a field potential U, $F_R = -\nabla(U)$, where the field potential U is defined as $$U = V_O \left[ \frac{\langle p^2(x,y,z) \rangle}{2\rho_f c_f^2} f_1 - \frac{3\rho_f \langle v^2(x,y,z) \rangle}{4} f_2 \right]$$

and $f_1$ and $f_2$ are the monopole and dipole contributions defined by $$f_1 = 1 - \frac{1}{\Lambda\sigma^2} \quad f_2 = \frac{2(\Lambda - 1)}{2\Lambda + 1}$$

where $$\sigma = \frac{c_p}{c_f} \quad \Lambda = \frac{\rho_p}{\rho_f} \quad \beta_f = \frac{1}{\rho_f c_f^2}$$

where p is the acoustic pressure, u is the fluid particle velocity, $\Lambda$ is the ratio of cell density $\rho_p$ to fluid density $\rho_f$, $\sigma$ is the ratio of cell sound speed $c_p$ to fluid sound speed $c_f$, $V_o = \pi R_p^3$ is the volume of the cell, and < > indicates time averaging over the period of the wave.

For a one dimensional standing wave, where the acoustic pressure is expressed as $$p = A \cos(kx)\cos(\omega t) \quad (4)$$

where A is the acoustic pressure amplitude, k is the wavenumber, and w is the angular frequency. In this case, there is only the axial component of the acoustic radiation force $F_{ARF}$, which is found to be $$F_{ARF} = V_O k X \frac{A^2}{4\rho_f c_f^2} \sin(2kx) \quad (5)$$

where X is the contrast factor given by $$X = \left( \frac{5\Lambda - 2}{1 + 2\Lambda} - \frac{1}{\sigma^2 \Lambda} \right)$$

Particles with a positive contrast factor will be driven to the pressure nodal planes, and particles with a negative contrast factor will be driven to the pressure anti-nodal planes. In this way, the generation of a multi-dimensional acoustic standing wave in an acoustic chamber results in the creation of tightly packed clusters of particles in the acoustic chamber, typically corresponding to the location of the pressure nodes or anti-nodes in the standing wave depending on acoustic contrast factor.

Gor'kov's model is for a single particle in a standing wave and is limited to particle sizes that are small with respect to the wavelength of the sound fields in the fluid and the particle. It also does not take into account the effect of viscosity of the fluid and the particle on the radiation force. As a result, this model cannot be used for macro-scale ultrasonic separators since particle clusters can grow quite large.

FIG. 1 is a log-log graph (logarithmic y-axis, logarithmic x-axis) that shows the scaling of the acoustic radiation force, fluid drag force, and buoyancy force with particle radius. Calculations are done for a typical mammalian cell used in experiments. In the experiment, the mammalian cell had a density ($\rho_p$) of 1,050 kg/m$^3$ and a cell sound speed ($c_p$) of 1,550 m/s. The fluid in which the particle was flowed was water having a density ($\rho_w$) of 1000 kg/m$^3$, a fluid sound speed ($c_f$) of 1500 m/s, and a flow rate ($v_f$) of 4 cm/min. The experiment used 33 PZT-8 ultrasonic transducers driven at a frequency (f) of 2.2 MHz at a pressure (p) of 1 MPa. As explained above, the gravity/buoyancy force is a particle volume dependent force, and is therefore negligible for particle sizes on the order of micron, but grows, and becomes significant for particle sizes on the order of hundreds of microns. The fluid drag force scales linearly with fluid velocity, and therefore typically exceeds the buoyancy force for micron sized particles, but is negligible for larger sized particles on the order of hundreds of microns. The acoustic radiation force scaling is different. When the particle size is small, Gor'kov's equation is accurate and the acoustic trapping force scales with the volume of the particle. Eventually, when the particle size grows, the acoustic radiation force no longer increases with the cube of the particle radius, and will rapidly vanish at a certain critical particle size. For further increases of particle size, the radiation force increases again in magnitude but with opposite phase (not shown in the graph). This pattern repeats for increasing particle sizes.

Initially, when a suspension is flowing through the system with primarily small micron sized particles, it is necessary for the acoustic radiation force to balance the combined effect of fluid drag force and buoyancy force for a particle to be trapped in the standing wave. In FIG. 1, this happens for a particle size of about 3.5 micron, labeled as $R_{c1}$. The graph then indicates that all larger particles will be trapped as well. Therefore, when small particles are trapped in the standing wave, particles coalescence/clumping/aggregation/agglomeration takes place, resulting in continuous growth of effective particle size. As the particle size grows, the acoustic radiation force reflects off the particle, such that large particles will cause the acoustic radiation force to decrease. Particle size growth continues until the buoyancy force becomes dominant, which is indicated by a second critical particle size, $R_{c2}$, at which size the particles will rise or sink, depending on their relative density with respect to the host fluid. Thus, FIG. 1 explains how small particles can be trapped continuously in a standing wave, grow into larger particles or clumps, and then continuously will rise or settle out because of enhanced buoyancy or gravity forces.

The models that were implemented in the present disclosure are based on the theoretical work of Yurii Ilinskii and Evgenia Zabolotskaya as described in AIP Conference Proceedings, Vol. 1474-1, pp. 255-258 (2012). These models also include the effect of fluid and particle viscosity, and therefore are a more accurate calculation of the acoustic radiation force.

The acoustophoretic separation technology of the present disclosure employs multi-dimensional ultrasonic acoustic standing waves, planar acoustic standing waves or combinations of planar and multidimensional acoustic standing waves (collectively referred to herein simple as acoustic standing waves) to trap particles or a secondary fluid in a volume of fluid containing said particles/secondary fluid.

Figures 2A, 2B:
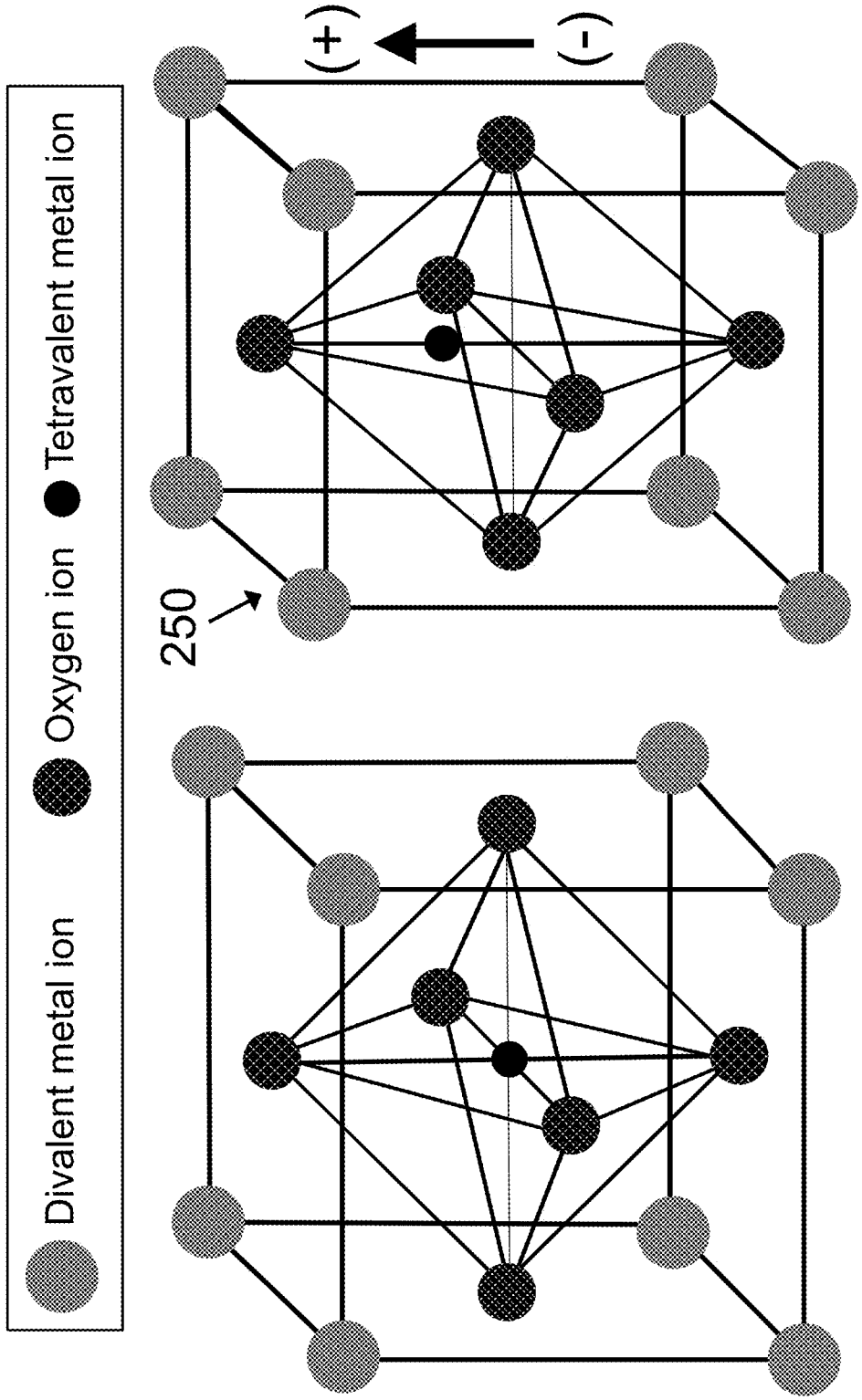
FIG. 2A illustrates a first embodiment of a piezoelectric material according to the present disclosure. The piezoelectric material is a perovskite crystal at a temperature above the Curie point.
FIG. 2B illustrates a second embodiment of a piezoelectric material according to the present disclosure. The piezoelectric material is a perovskite crystal at a temperature below the Curie point.

Turning now to FIG. 2A, a first embodiment of a piezoelectric material 200 is shown. In the embodiment depicted in FIG. 2A, the piezoelectric material 200 is a perovskite crystal at a temperature above the Curie point. The piezoelectric material 200 is in the shape of a cubic lattice with a symmetrical arrangement of positive and negative charges. FIG. 2B shows a second embodiment of a piezoelectric material 250. In the embodiment depicted in FIG. 2B, the piezoelectric material 250 is a perovskite crystal at a temperature below the Curie point. The piezoelectric material 250 is in the shape of a tetragonal (orthorhombic) lattice with an electric dipole. Both of the piezoelectric materials 200, 250 depicted in FIG. 2A and FIG. 2B are comprised of divalent metal ion(s) (e.g., lead, barium), oxygen ion(s), and tetravalent metal ion(s) (e.g., titanium, zirconium). The dipole expansion and contraction of the piezoelectric materials 200, 250 depicted in FIG. 2A and FIG. 2B allow for the piezoelectric effect to occur, resulting in the generation of pressure waves.

The Curie point is a critical temperature at which each perovskite crystal in a piezoelectric material exhibits a simple cubic symmetry with no dipole moment. However, at temperatures below the Curie point, such as is depicted in FIG. 2B, each crystal has tetragonal or rhombohedral symmetry and a dipole moment. Adjoining dipoles form regions of local alignment are called domains. The alignment of the crystals gives a net dipole moment to the domain in the crystal and, as a result, generates a net polarization. The polarization, however, is still random and thus there is no overall direction that the piezoelectric crystal will change in shape when an electrical impulse is applied.

In operation, a strong, direct current electric field, usually at a temperature slightly below the Curie point, is applied to the crystal. Through this poling (polarization) treatment, the domains of the piezoelectric crystal most nearly aligned with the electric field expand at the expense of domains that are not aligned with the field, and the piezoelectric crystal expands in the direction of the strong electrical field. When the electric field is removed, most of the dipoles are locked into a configuration of near alignment. The piezoelectric crystal now has a permanent polarization (i.e., the crystal can be considered "poled"). Thus, upon supplying an electrical charge to the crystal, the crystal will expand and contract in the direction that it is now poled.

In a conventional flat/planar piezoelectric surface, a single frequency can be used to excite a multi-dimensional acoustic standing wave. In accordance with the present disclosure, it has been found that a piezoelectric material having a non-planar (i.e., non-flat) face can be electrically excited by a single frequency to further enhance the expansion and contraction in the poled direction of the crystal, such that differential vibrations (as opposed to uniform vibrations) emanate from the surface of the non-planar face of the piezoelectric material to generate a multi-dimensional acoustic standing wave. Through proper shaping of the non-planar surface, a multi-dimensional acoustic standing wave can be generated as desired (e.g., with a desired strength, shape, intensity).

Figure 3:
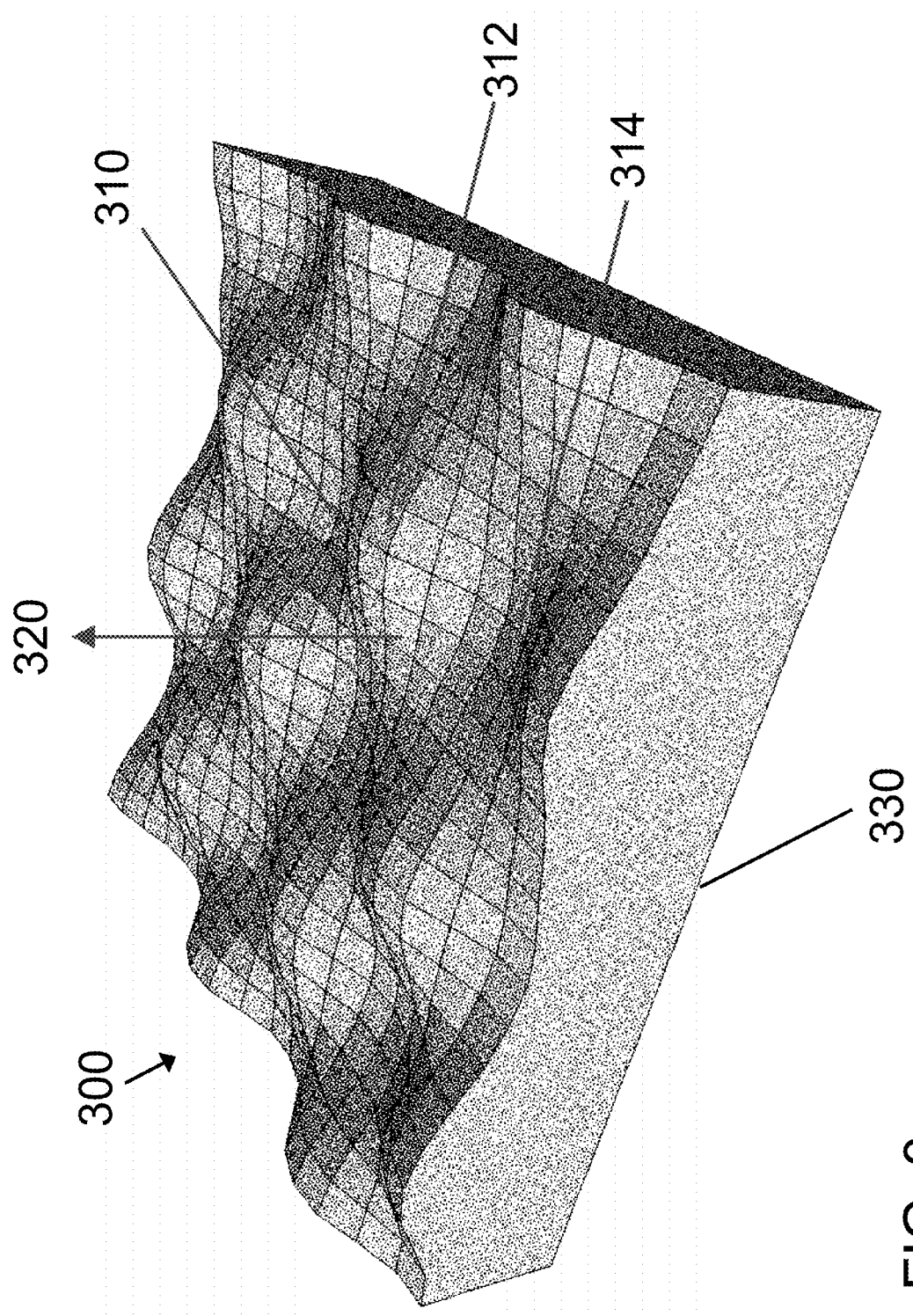
FIG. 3 illustrates a first embodiment of a non-planar face of a piezoelectric material according to the present disclosure. The non-planar face of the piezoelectric material is defined by a smooth function.

FIG. 3 shows a first embodiment of such a piezoelectric material 300 in which a non-planar first face 310 of the piezoelectric material 300 is defined by a smooth function. In this way, the non-planar face 310 of the piezoelectric material 300 is poled in a direction 320 substantially perpendicular to a second face 330 of the piezoelectric material 300. In the piezoelectric material 300 depicted in FIG. 3, the non-planar face 310 and the second face 330 are located on opposite sides of the crystal. The second face is planar, and provides the reference against which the non-planarity of the first face 310 is determined. As seen here, the first face 310 is formed from a series of peaks 312 and valleys 314. The transition between the peaks and valleys is smooth. A smooth function is a function having a derivative that is continuous.

A single electrode can be used on each side of the piezoelectric material. The electrode may be coated by several means, such as plating with electroless nickel or spray coating with a conductive coating, such as a silver-containing coating. The electrodes must be separated so that there is a positive terminal and a negative terminal to energize the piezoelectric material.

Figure 4:
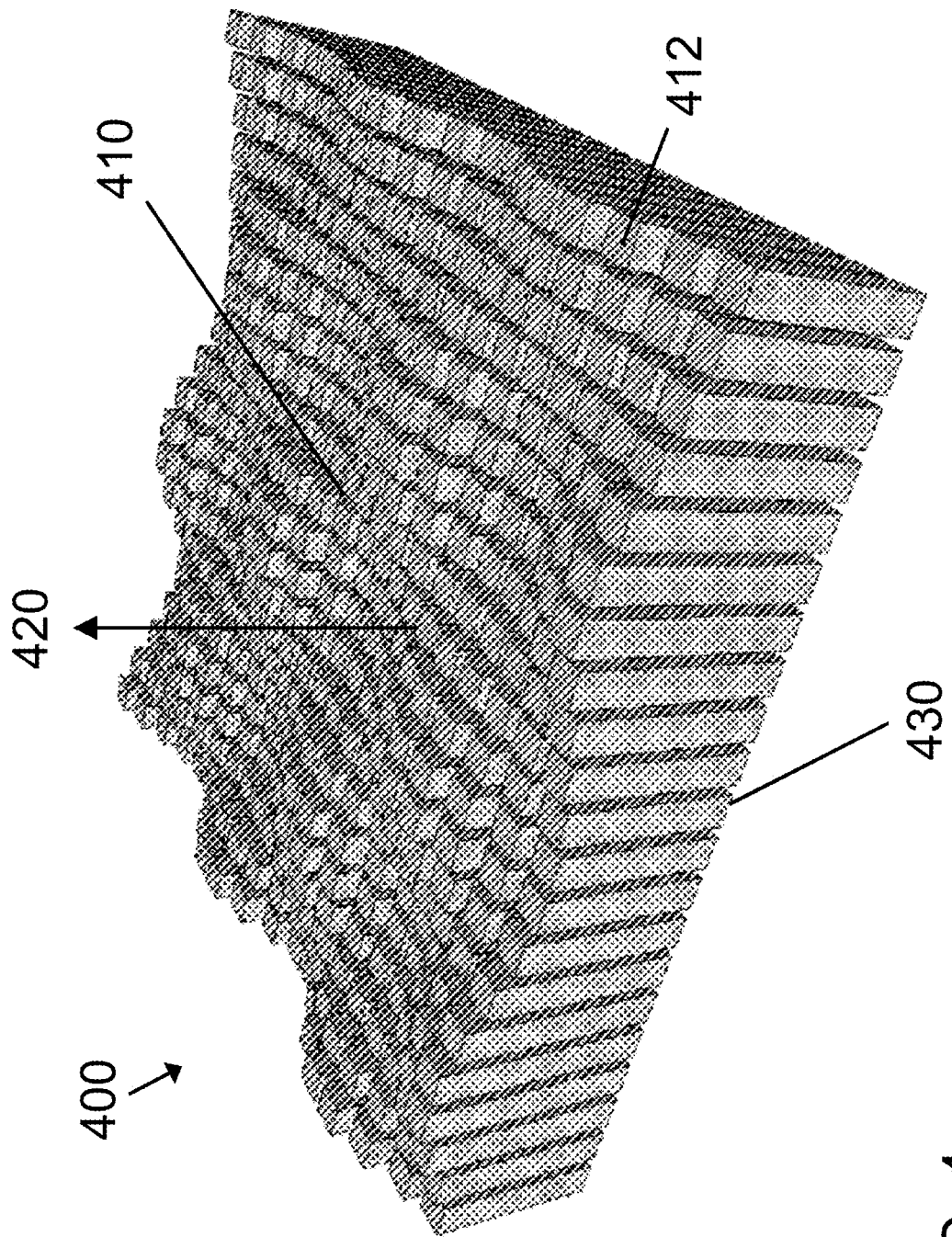
FIG. 4 illustrates a second embodiment of a non-planar face of a piezoelectric material according to the present disclosure. The non-planar face of the piezoelectric material is defined by a stepped function formed by facets.

In contrast to FIG. 3, FIG. 4 shows a second embodiment of a piezoelectric material 400 in which a non-planar first face 410 of the piezoelectric material 400 is defined by a stepped function. Again, the non-planar face 410 of the piezoelectric material 400 is poled in a direction 420 substantially perpendicular to a second face 430 of the piezoelectric material 400. A stepped function is a piecewise constant function. As seen here, the overall shape of the first face 410 is made up of a series of smaller flat surfaces 412, also referred to herein as facets.

Figure 5:
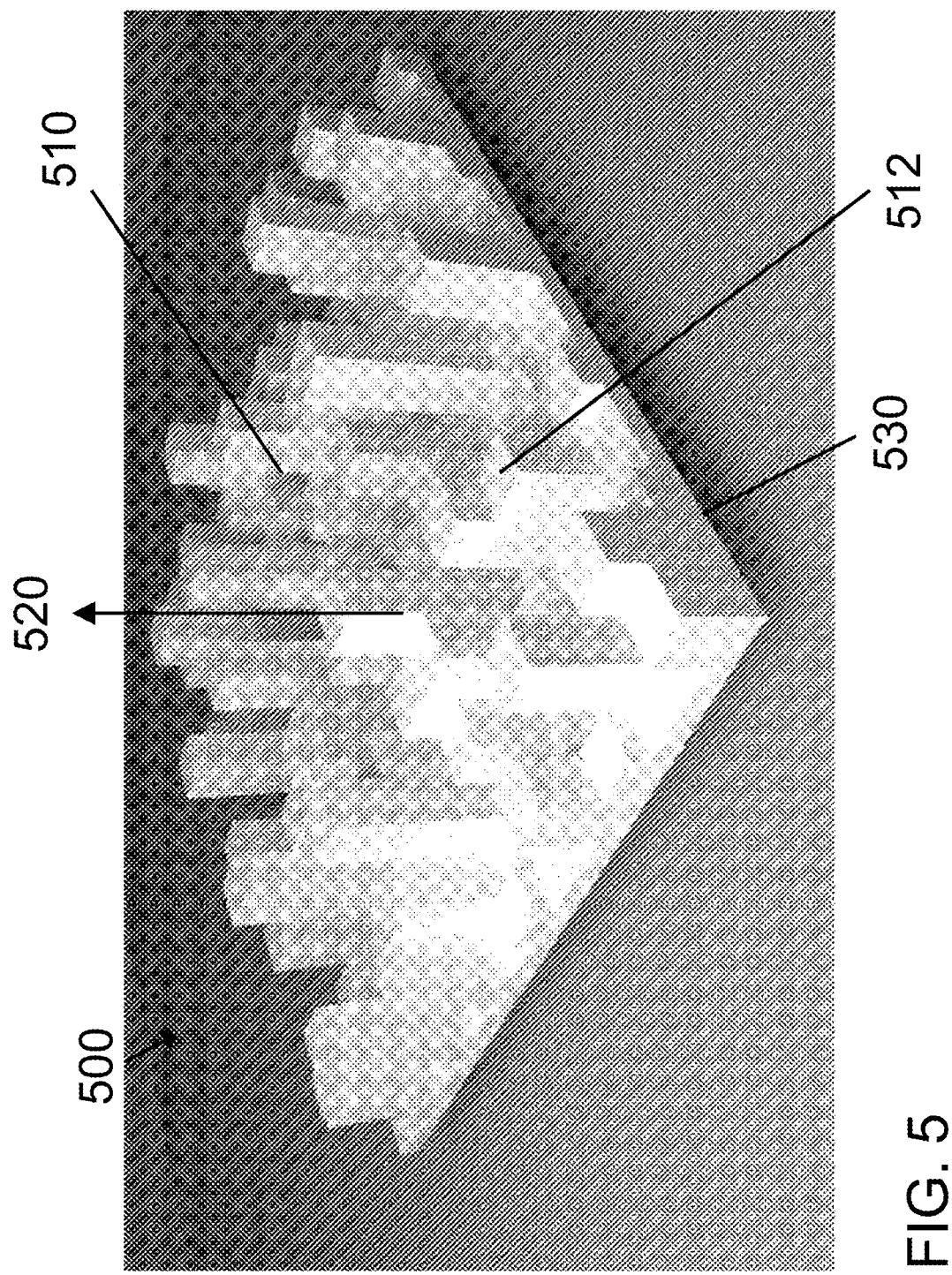
FIG. 5 illustrates a third embodiment of a non-planar face of a piezoelectric material according to the present disclosure. The non-planar face of the piezoelectric material is defined by a stepped function formed by facets.

FIG. 5 shows a third embodiment of a piezoelectric material 500 in which a non-planar face 510 of the piezoelectric material 500 is defined by a stepped function. Yet again, the non-planar first face 510 of the piezoelectric material 500 is poled in a direction 520 substantially perpendicular to a second face 530 of the piezoelectric material 500. The main difference between FIG. 4 and FIG. 5 is that the adjacent smaller flat surfaces 512 (i.e. facets) vary much more in their difference in height (relative to the second face 530).

Figure 6:
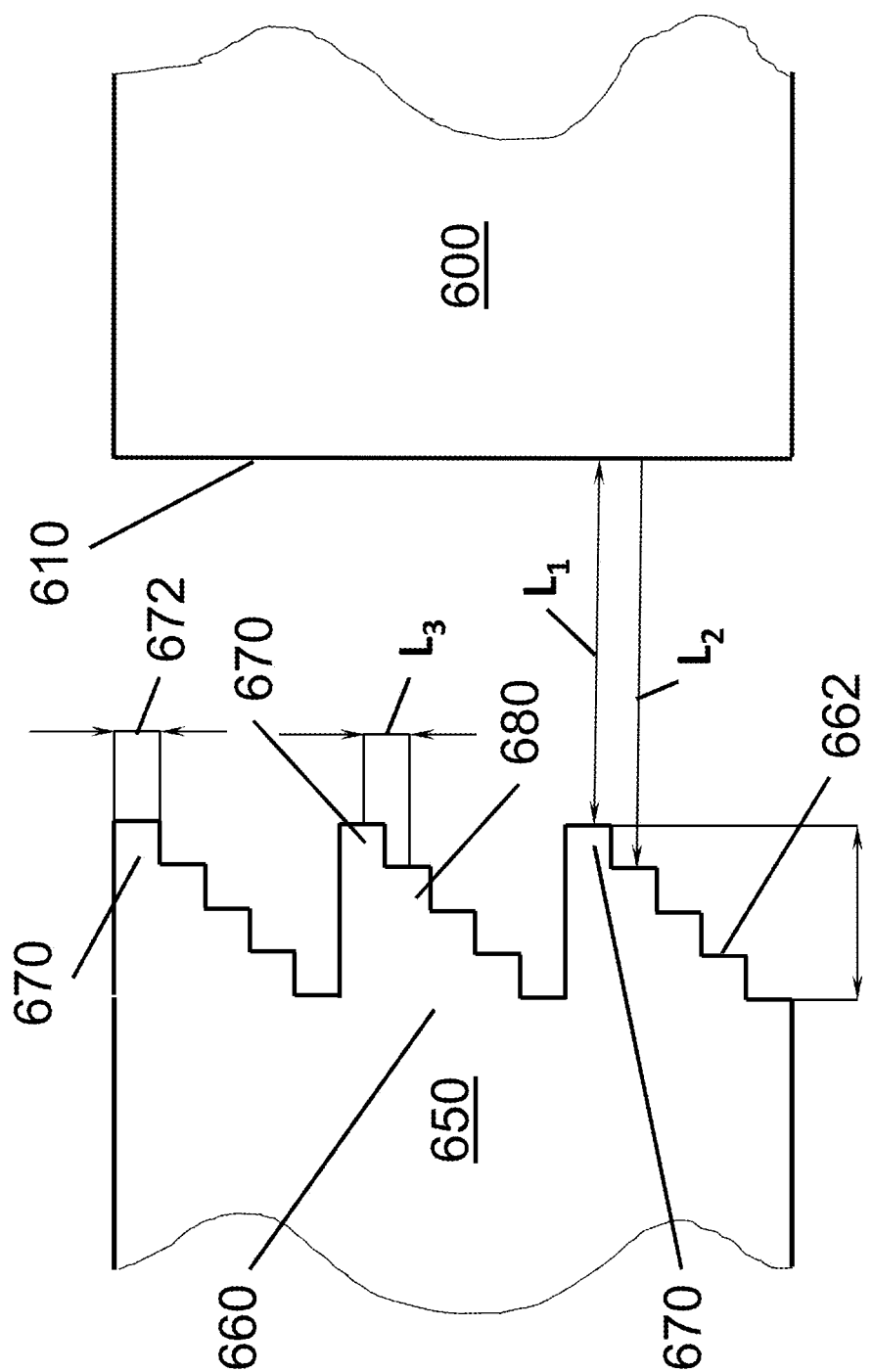
FIG. 6 illustrates a cross-sectional view of an acoustic chamber of an acoustophoretic device according to the present disclosure. The device includes a piezoelectric material having a planar first face and a reflector having a faceted surface.

It is also contemplated that the reflector located on an opposite side of the acoustic chamber from the transducer/piezoelectric material can also have a non-planar surface, which can be likewise defined by a smooth or stepped function. The non-planar face of the transducer/piezoelectric material and the non-planar surface of the reflector may be described as being faceted, such as is depicted in FIG. 6. In FIG. 6, the piezoelectric material 600 has a flat, planar first face 610, and the reflector 650 has a faceted surface 660. The faceted surface 660 of the reflector 650 is defined by flat surfaces or facets 662, similar to the facets 512 of the piezoelectric material 500 of FIG. 5 and the facets 412 of the piezoelectric material 400 of FIG. 4. That is, as depicted in FIG. 6, the facets 662 in the faceted surface 660 of the reflector 650 can be stepped, such that adjacent facets are located different distances from a first face 610 of the piezoelectric material 600. For example, facet 670 is located distance $L_1$ from the first face 610 of the piezoelectric material 600, while facet 680 is located distance $L_2$ from the first face 610 of the piezoelectric material 600, with $L_1$ being greater than $L_2$. It is to be understood that the facets 662 may be dimensioned as desired. For example, facet 670 typically has a width 672 selected to maximize the reflected energy. Similarly, the distance between adjacent facets, such as distance $L_3$ between facet 670 and facet 680, is typically selected to minimize the distance between the director of a natural vibration mode of the piezoelectric material and adjacent facets. The distance between a facet and the first face 610 of the piezoelectric material 600 (e.g., distance $L_1$ for facet 670 and distance $L_2$ for facet 680) typically corresponds to a half wavelength to accommodate for all possible resonance conditions in the acoustic chamber.

Figure 7A:
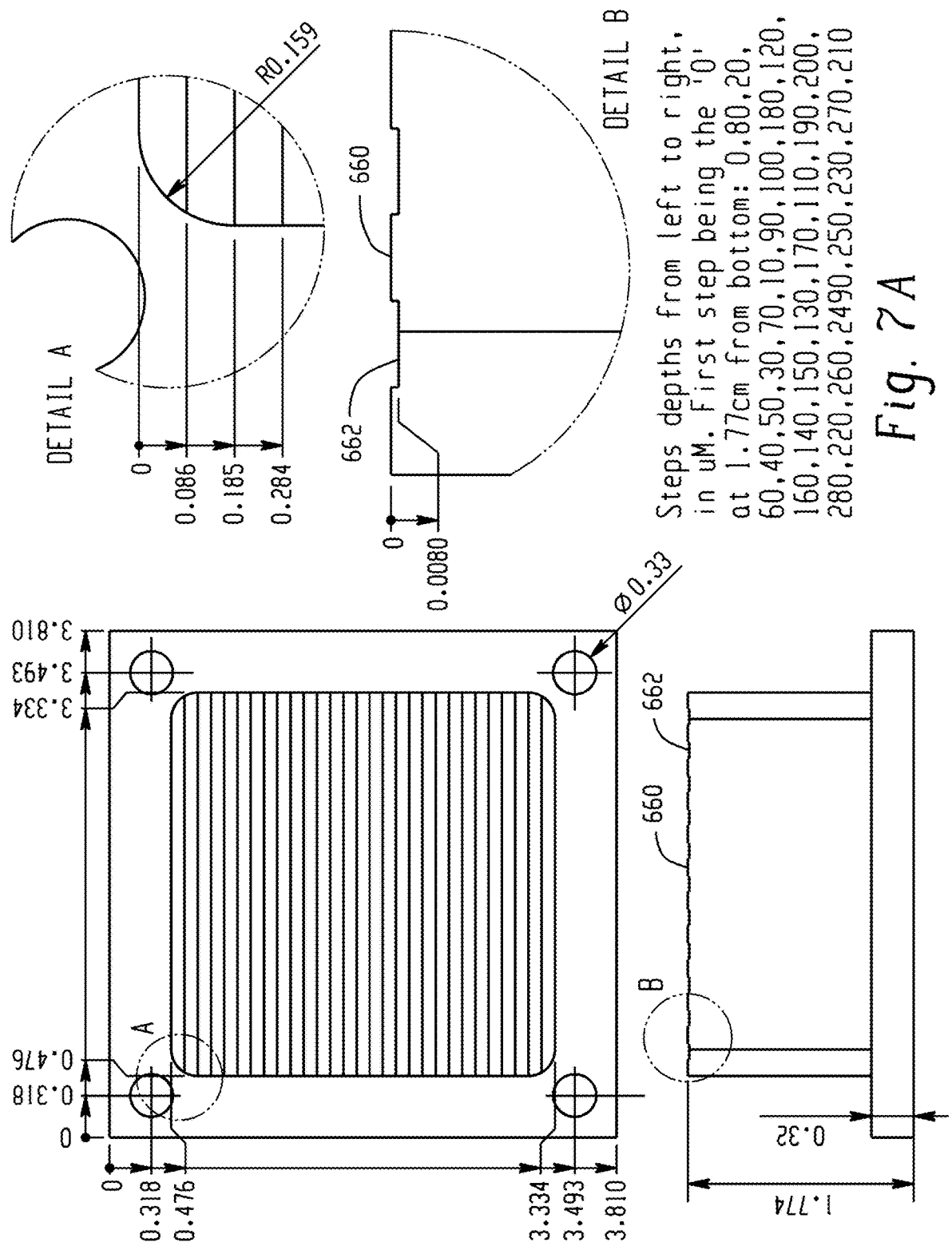
FIG. 7A illustrates a first exemplary configuration of the faceted surface of the reflector of FIG. 6.
Figure 7B:
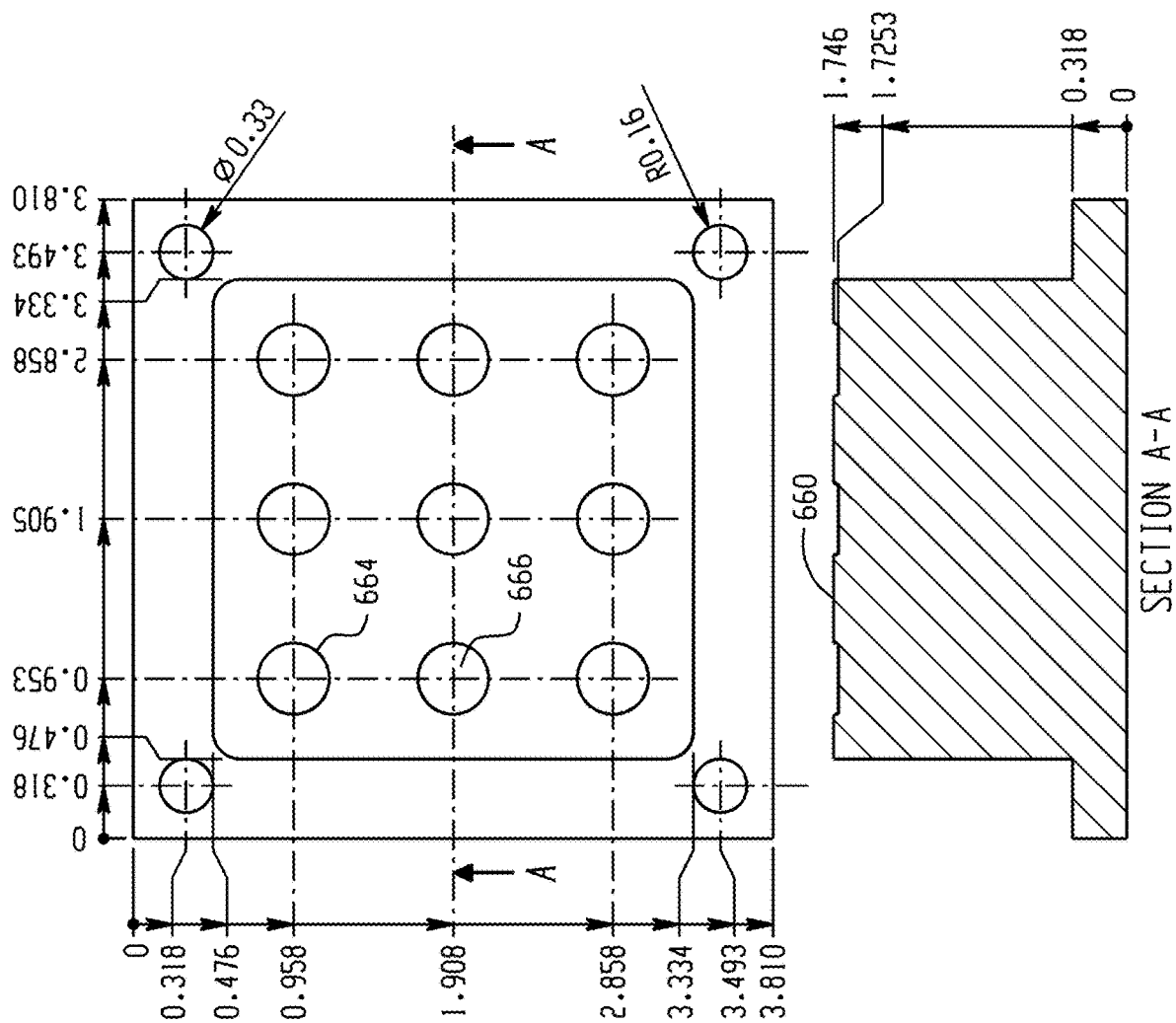
FIG. 7B illustrates a second exemplary configuration of the faceted surface of the reflector of FIG. 6.

As will be appreciated by those skilled in the art, the facets 662 can be arranged as desired to create an acoustic standing wave having a desired mode pattern. FIGS. 7A-7C depict various exemplary configurations of the faceted surface 660 of the reflector 650. For example, FIG. 7A shows a design in which the faceted surface 660 of the reflector 650 includes flat surfaces or facets 662 that extend along the length of the reflector 650. The height of a given facet generally differs from the height of an adjacent facet by a fraction of the generated acoustic standing wave. The design in FIG. 7A implements a degenerated one-dimensional pattern of intermittent steps.

FIG. 7B shows a design in which the faceted surface 660 of the reflector 650 includes wells 664 having flat bottoms 666. In the exemplary embodiment of FIG. 7B, the wells 664 are all of equal depth. The distribution of the wells 664 on the faceted surface 660 of the reflector 650 corresponds to the distribution of the 3×3 mode pattern emitted by the reflector 650. The wells are distributed in a regular pattern along the faceted surface.

Figure 8:
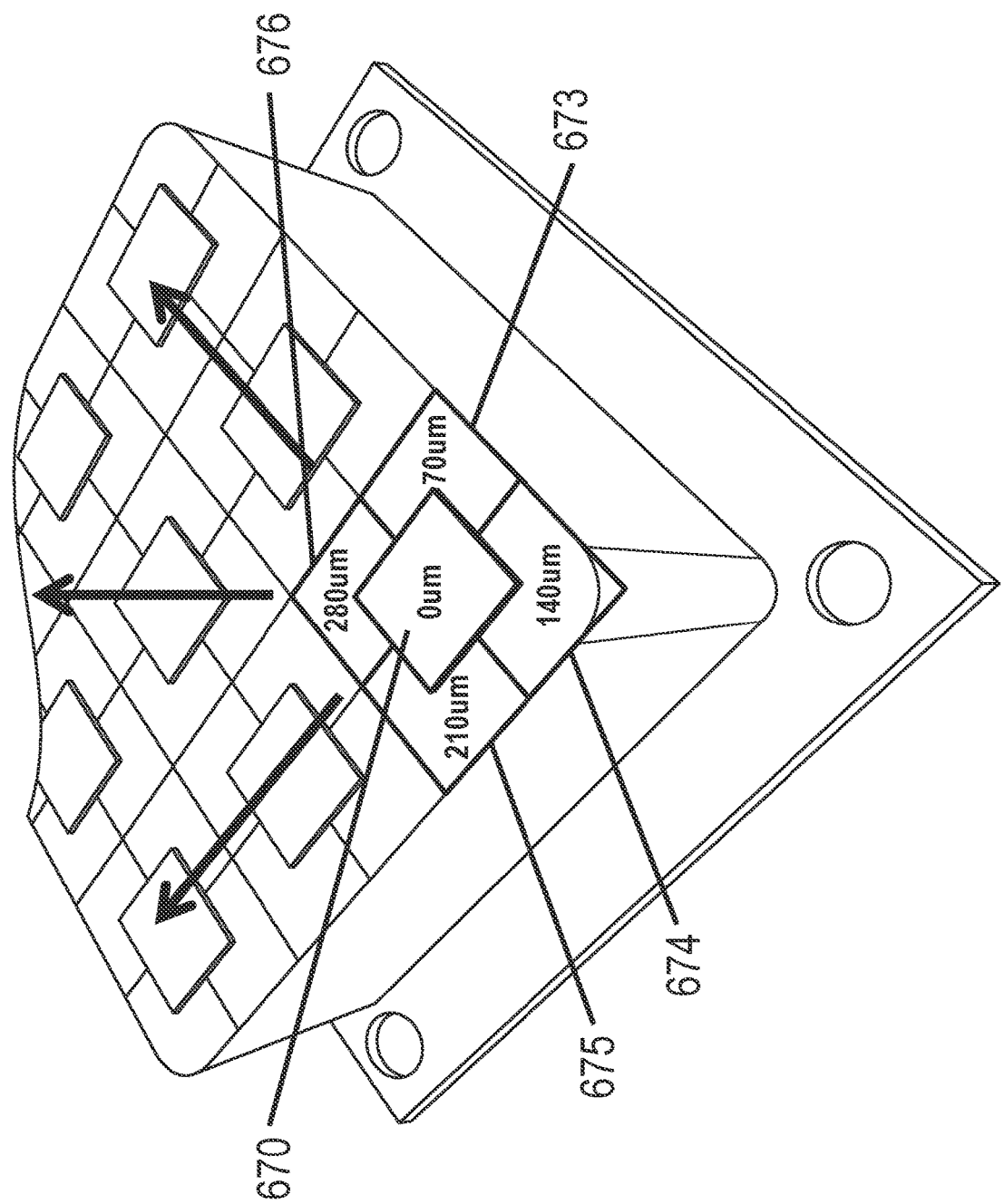
FIG. 8 illustrates a magnified view of a facet cluster of the faceted surface of FIG. 7C, showing the height differential between a central facet and four surrounding outer facets.

Finally, FIG. 7C and FIG. 8 show a design in which the faceted surface 660 of the reflector 650 includes multiple facet clusters 668. In this exemplary embodiment, each facet cluster 668 is comprised of a pyramid-shaped group of five facets, with four outer facets 673, 674, 675, 676 differing from a central facet 670 by a multiple of 0.1 wavelengths. That is, if the central facet 670 corresponds to the 0 position, the four outer facets 673, 674, 675, 676 are deeper by 0.1, 0.2, 0.3, and 0.4 wavelengths, respectively. For example, central facet 670 in FIG. 8 corresponds to position 0, outer facet 673 is located 70 μm below the surface of the central facet 670, outer facet 674 is located 140 μm below the surface of the central facet 670, outer facet 675 is located 210 μm below the surface of the central facet 670, and outer facet 676 is located 240 μm below the surface of the central facet 670. The distribution of the facet clusters 668 corresponds to the distribution of the 9×9 mode pattern reflected by the reflector, though it is to be understood that such a design could also be used with a 3×3 mode pattern. It is further contemplated that the pattern of the facets in the faceted surface 660 of the reflector 650 may influence the mode selection for various frequencies. The number of facets or facet levels within a single facet cluster is typically selected to ensure smooth adjustment to the changing resonance conditions within the acoustic chamber (i.e., more facets or facet levels for more gradual transitions), with the facets or facet levels differing from one another by a fraction of the acoustic wavelength, as previously explained. The number of facets or facet levels should, however, generally be limited to minimize the total number of facets, thereby increasing the reflecting area per facet. As will be appreciated by those skilled in the art, the piezoelectric material may likewise have a faceted front face, similar to the faceted surface of the reflector depicted in FIG. 6 and FIGS. 7A-7C. In such embodiments, the first face of the piezoelectric material is faceted, while the surface of the reflector is generally kept planar or flat.

Figure 9:
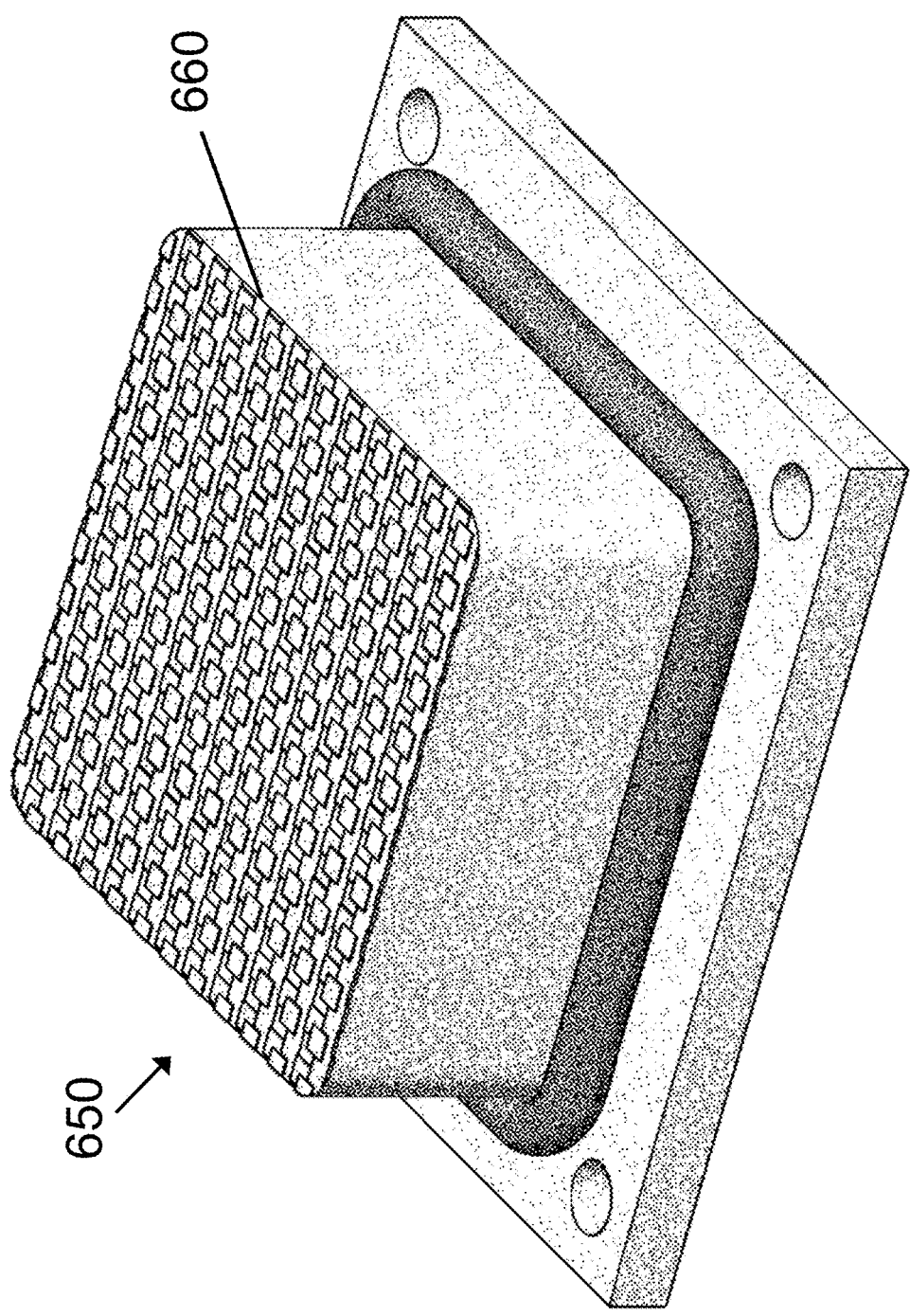
FIG. 9 illustrates a fourth exemplary configuration of the faceted surface of the reflector of FIG. 6.
Figure 10:
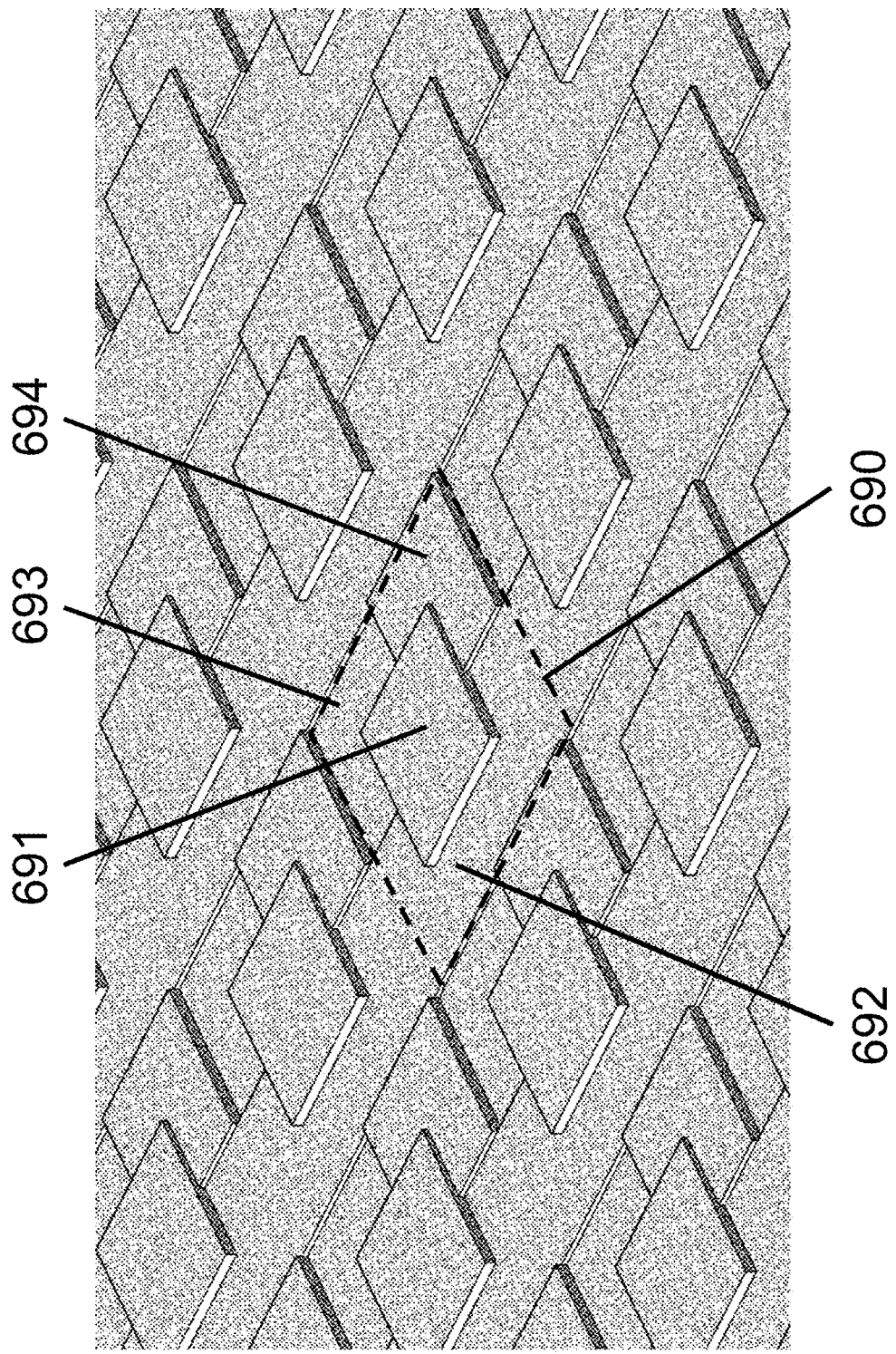
FIG. 10 illustrates a magnified view of the faceted surfaces depicted in FIG. 9.

FIG. 9 and FIG. 10 depict another exemplary embodiment of a faceted surface 660 of the reflector 650. FIG. 9 shows the entire reflector, while FIG. 10 provides a magnified view of a portion of the faceted surface 660 of the reflector 650. As best seen in FIG. 10, the surface is divided into multiple facets that provide four different heights. A dotted line is used to indicate the facet cluster 690. The central facet 691 is surrounded by a second facet 692, a third facet 693, and a fourth facet 694. The second facet 692 has approximately twice the surface area of the third facet or the fourth facet. The third facet 693 is the lowest of these facets, followed by the second facet 692, then the fourth facet 694, with the central facet 691 being the highest of these facets.

It is noted that in FIGS. 4-10, the facets are generally illustrated as being surfaces with a square-shaped perimeter. This is not a requirement, and the facets may be of any suitable shape, e.g. rectangular, circular, etc.

As will be explained in greater detail herein, the operation of the acoustophoretic devices of the present disclosure includes generation of acoustic standing waves in an acoustic chamber. The acoustic standing waves can be at a fixed frequency throughout the period of operation, and the frequency may be selected to match the mode distribution of the piezoelectric material to the facet distribution of the reflector. The maximal amplitude of the acoustic standing wave is achieved under the resonance conditions that occur when the wave frequency f satisfies the condition $f=nc/2L$, where c is the speed of sound in the medium, n is a positive integer, and L is the distance between the transducer and the reflector. Optimal cell separation is achieved under the resonance conditions at the maximal amplitude of the acoustic pressure for a fixed emitter power. The maximal acoustic pressure in turn leads to the maximal acoustic radiation force, which is the result of the acoustic field gradients, and to the most efficient cell trapping. When particles (e.g., cells) accumulate within the acoustophoretic device (or more generally due to inhomogeneous conditions), the speed of sound c changes and the resonance conditions are destroyed. The speed of sound may also change due to the change of temperature of the suspension. The temperature change may be a result of the acoustic operation or due to the change of the feed solution temperature. The resonance conditions can be changed also for different suspension compositions. These are most typical, but not all the possible, mechanisms of the resonance destruction.

Figure 11:
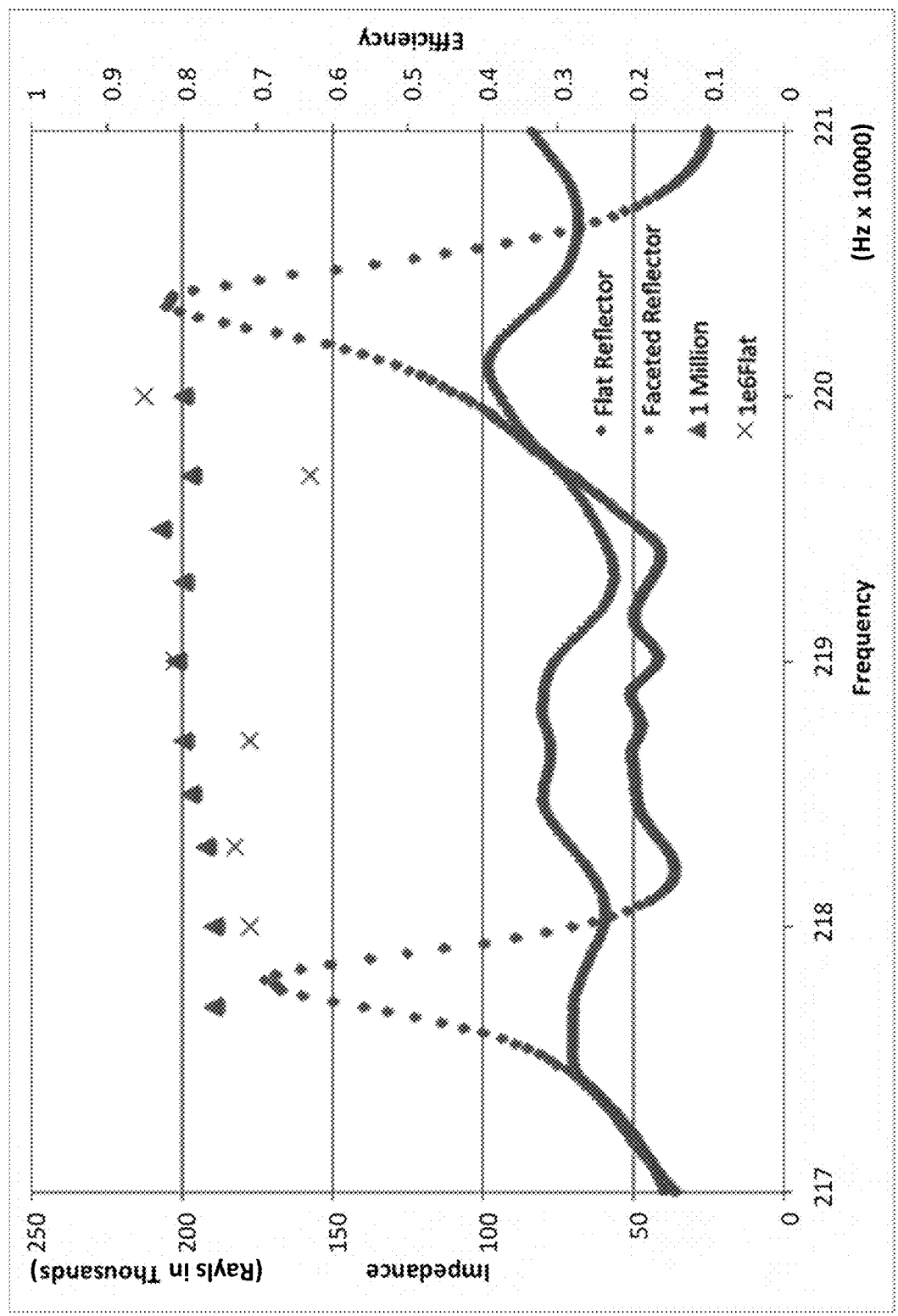
FIG. 11 is a graph illustrating the separation efficiency of a faceted reflector versus a flat, planar reflector at varied impedance levels. The left-hand y-axis is impedance in thousands of rayls. The two lines marked as "flat reflector" and "faceted reflector" are read against the left-hand y-axis. The right-hand y-axis is efficiency. The points labeled "1 mission" and "1e6 flat" (triangular and X-shaped points) are read against the right-hand y-axis. The x-axis is in units of ten thousand Hertz.
Figure 12:
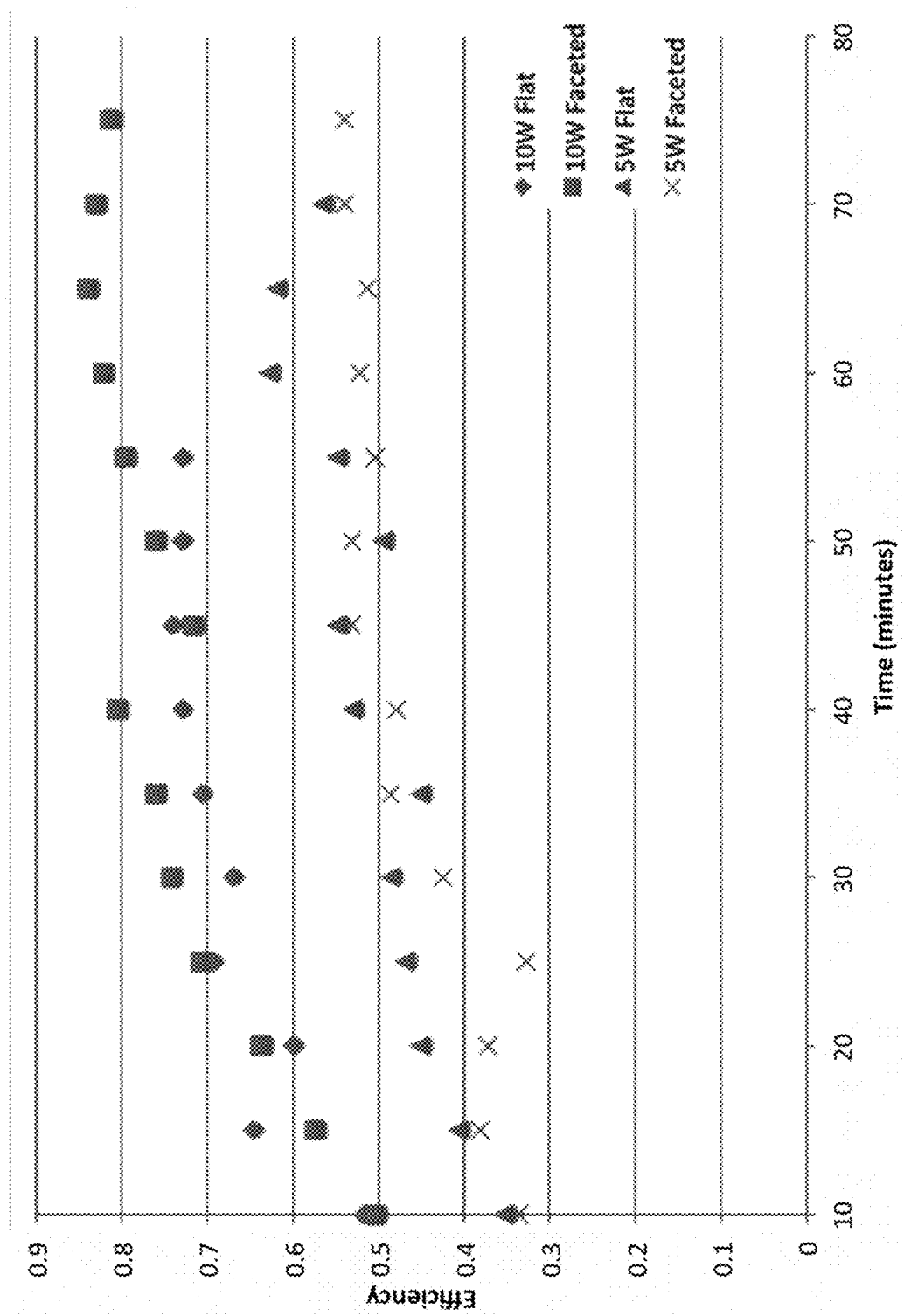
FIG. 12 is a graph illustrating the separation efficiency of a faceted reflector versus a flat, planar reflector over time at a frequency of 2.185 MHz and two different powers (5W and 10W).

FIG. 11 graphically illustrates some of the advantages of using a reflector having a faceted surface over a flat, planar reflector. In FIG. 11, the lowest two lines (i.e., the lines having square and diamond-shaped points) represent the impedance of a faceted reflector and flat reflector in thousands of Rayls along the left y-axis, and the upper two lines (i.e., the lines having triangular and X-shaped points) represent the efficiency of a faceted reflector and a flat reflector in values of percentage along the right y-axis. The x-axis of FIG. 11 represents various operating frequencies in ten thousands of Hertz. FIG. 11 shows that for a yeast concentration of $1\times10^6$ cells/mL, the efficiency of a faceted reflector was noticeably greater than the efficiency of a flat, planar reflector. A similar result is noticed in FIG. 12, which graphically illustrates the efficiency of a faceted reflector versus the efficiency of a flat, planar reflector at a frequency of 2.185 MHz across a period of 80 minutes.

Referring back to FIG. 6, when the resonance is destroyed for facet 670 separated by distance $L_1$ from the piezoelectric material 600, the standing wave "hops" to nearby facet 680, which corresponding $L_2$ distance from the piezoelectric material 600 satisfies the resonance conditions at the new speed of sound. Therefore, the device is a self-tuning system capable of readjusting to maintain a strong multi-dimensional (e.g., three-dimensional) acoustic field regardless of the changing properties of the processed suspension, and capable of working at the same operation frequency. Put another way, the use of a reflector having a faceted surface improves the acoustophoretic device by shortening or completely eliminating the undesirable time periods during which the frequency of the device must be scanned and, therefore, out of tune.

The use of a reflector having a faceted surface also optimizes the performance at uneven cell mass distribution. As the cell density and concentration can be different along the paths between the piezoelectric material/transducer and the reflector at different positions across the resonator cross section, the resonance conditions can be different along these paths. With a reflector having a faceted surface, different facets are available to re-tune the resonator along these paths in accordance to these local conditions. This level of optimization does not exist in a flat transducer-flat reflector system, even with agile frequency tuning.

Moreover, the use of a reflector having a faceted surface suppresses the standing wave corresponding to the "piston" mode of the flat piezoelectric material/transducer regardless of the frequency. Therefore, the range of operation frequencies available with the reflector having a faceted surface is wider than with a flat transducer-flat reflector system.

The differential vibrations of the non-planar face of the piezoelectric material allow for differential pressure waves to be generated from the non-planar face of the piezoelectric material using a single voltage input from the function generator and the amplifier into the piezoelectric material. This, in turn, allows for the creation of a multi-dimensional acoustic standing wave and further allows for local wave fronts with varying amplitudes to come from the non-planar face of the piezoelectric material with a single frequency input to then generate the multi-dimensional standing wave in the fluid.

Figure 13:
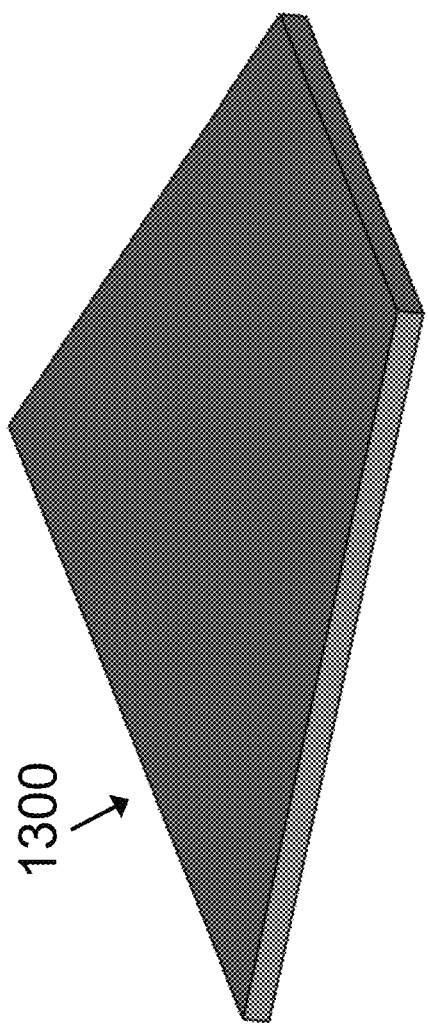
FIG. 13 illustrates a third embodiment of a piezoelectric material according to the present disclosure. The piezoelectric material has a non-symmetrical, trapezoidal shape.
Figure 14A:
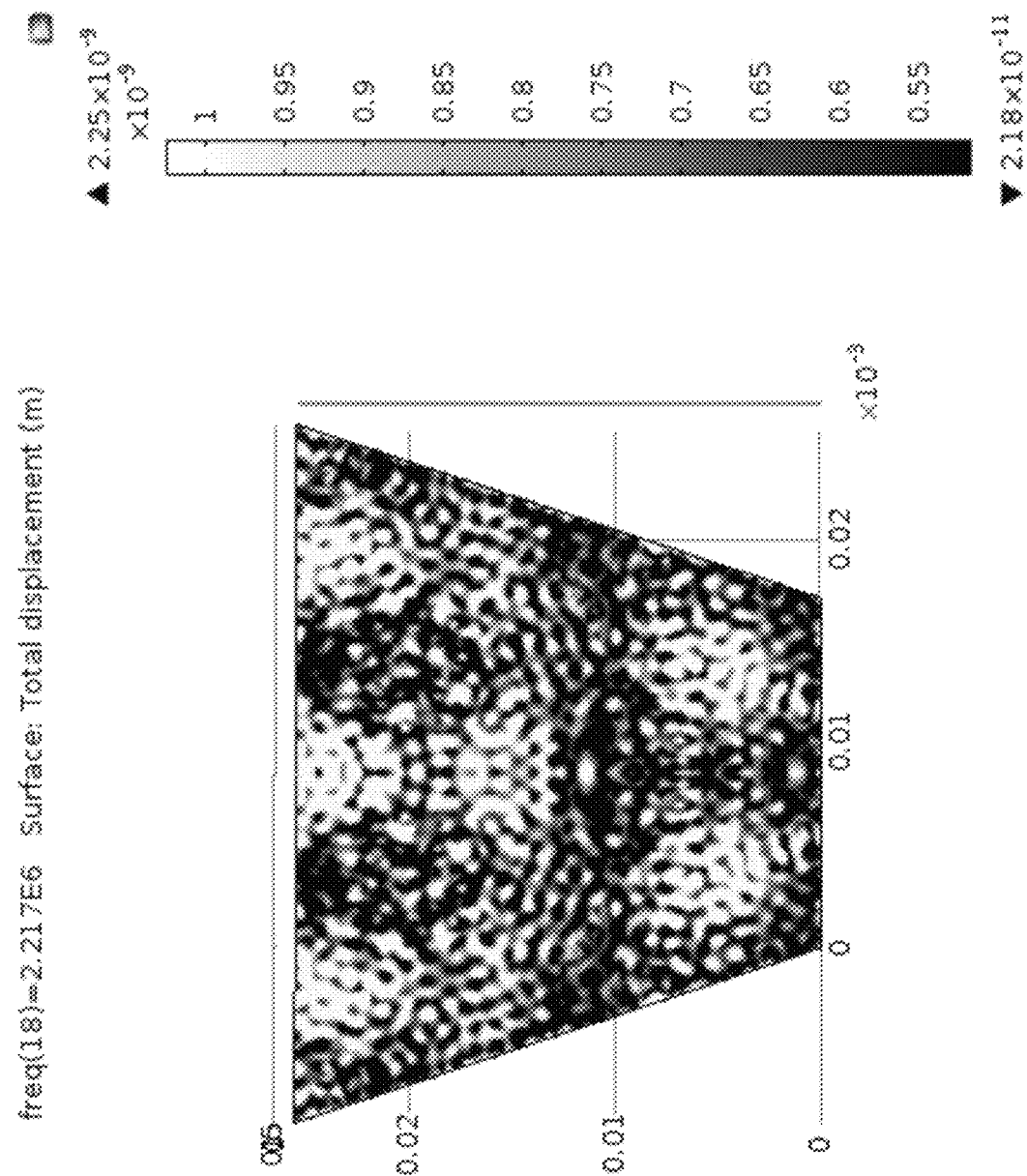
FIGS. 14A-14D illustrate the non-planar face of the trapezoidal piezoelectric material of FIG. 13 upon which asymmetric excitation patterns are generated at four different frequencies.
Figure 14B:
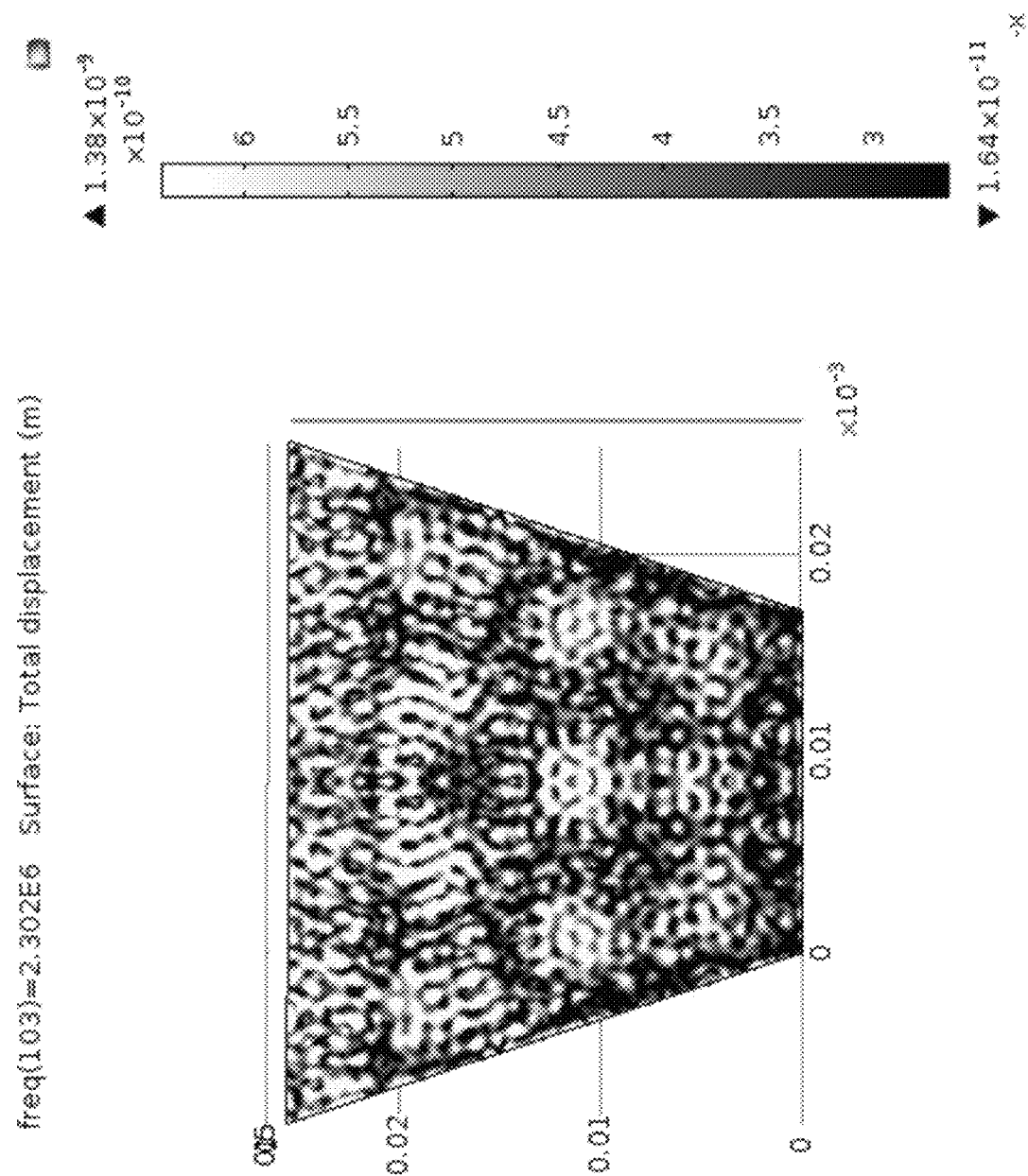
Figure 14C:
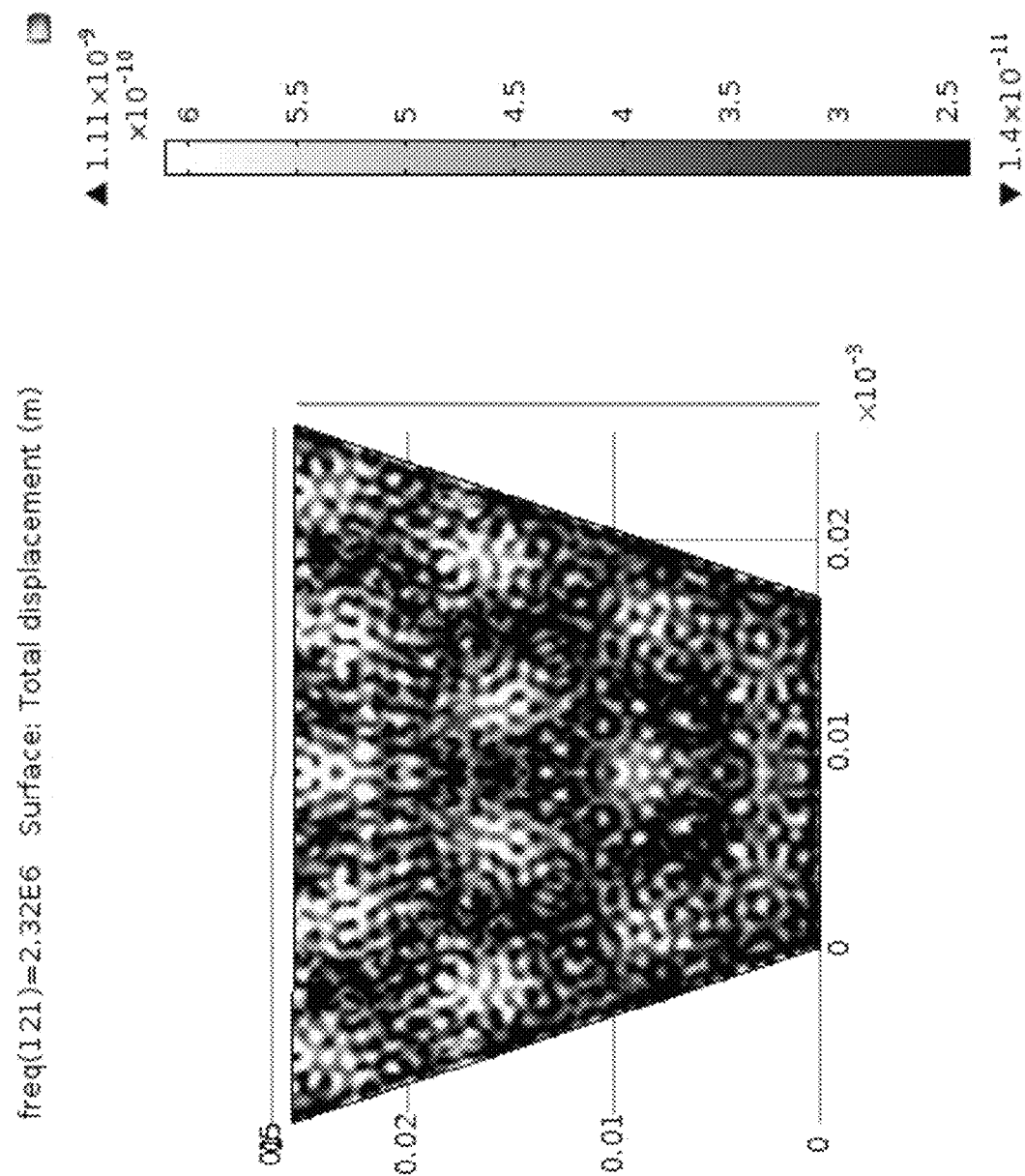
Figure 14D:
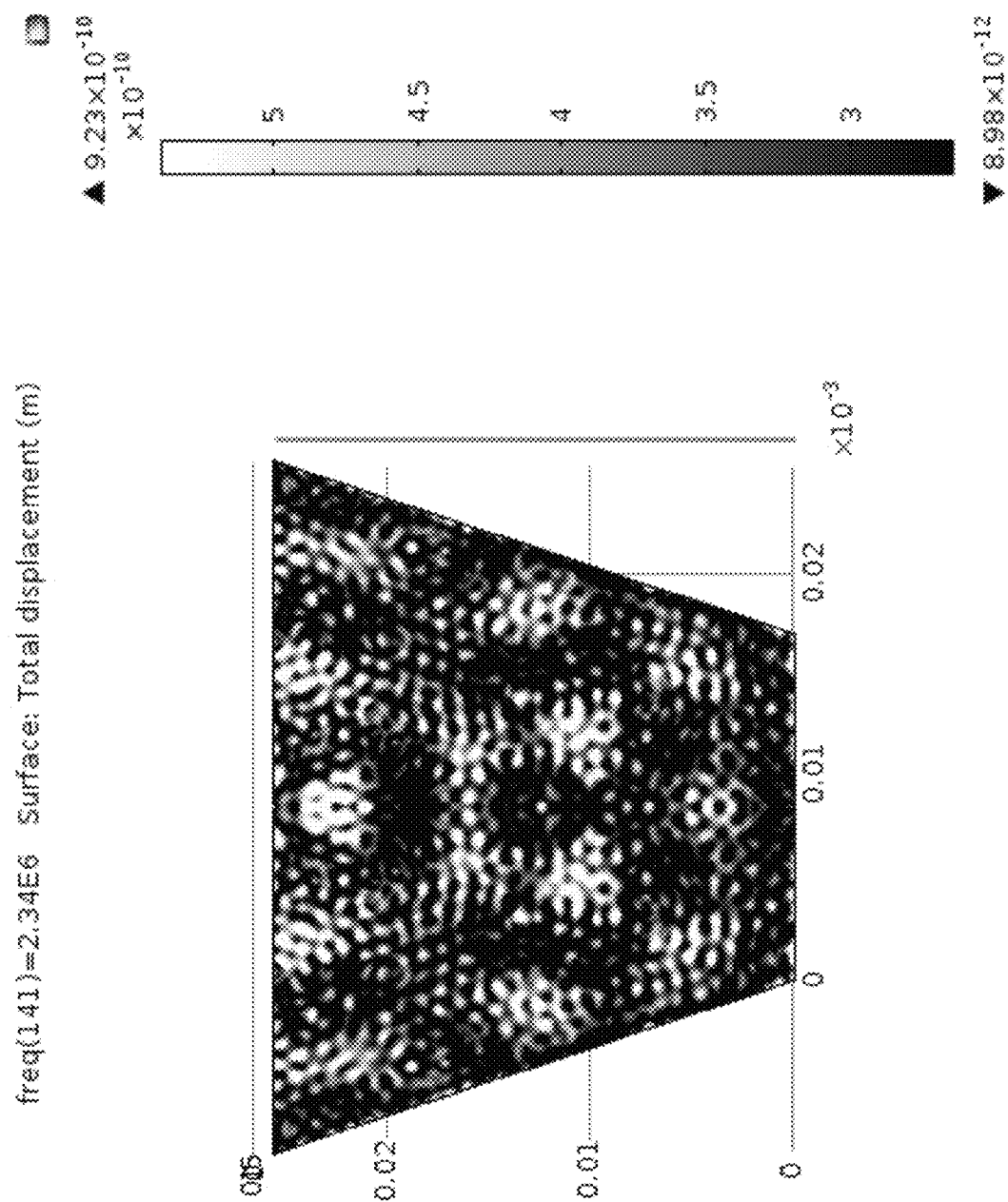

In certain embodiments, the piezoelectric material and/or reflector may be non-symmetrical or asymmetric in shape. This refers to the shape of the piezoelectric material as defined by its perimeter. Put another way, the perimeter of the piezoelectric material forms an irregular polygon, or the piezoelectric material does not have any axis of symmetry. The piezoelectric crystal of FIG. 3, for example, is a square, which is symmetrical. However, piezoelectric material 1300 depicted in FIG. 13 has a trapezoidal shape with four different angles. Designing the piezoelectric material to have a non-symmetrical shape allows for an acoustic standing wave created by the piezoelectric material to generate trapping lines that are asymmetric.

FIGS. 14A-14D show four asymmetric excitation patterns generated on the face of a trapezoidal piezoelectric material at four different frequencies. The asymmetry of the piezoelectric material leads to generation of asymmetric trapping lines of particles inside the fluid, at different frequencies of excitation. This asymmetric field of trapping lines allows for less interference between adjacent trapping lines when continuous gravity separation of a secondary fluid or particulate from a host fluid is in operation. Put another way, when a non-symmetrical piezoelectric material is placed in an acoustic chamber across from a reflector having a non-symmetrical or another shape, the trapping lines of the standing wave will be staggered in such a manner that the collected secondary fluid or particles in each trapping line interfere less with one another as they are gravitationally separated from the host fluid, compared to those generated by a symmetric piezoelectric material.

In accordance with the present disclosure, the particles or secondary fluid collect at the nodes or anti-nodes of the acoustic standing wave, depending on the particles' or secondary fluid's acoustic contrast factor relative to the host fluid, forming clusters/clumps/agglomerates/coalesced droplets that continuously fall out of the acoustic standing wave when the clusters have grown to a size large enough to overcome the holding force of the acoustic standing wave (e.g. by coalescence or agglomeration) and the particle/secondary fluid density is higher than the host fluid, or to rise out of the acoustic standing wave when the particle/secondary fluid density is less than the host fluid. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). For harmonic excitation, the sinusoidal spatial variation of the force is what drives the particles to the stable axial positions within the standing waves. When the acoustic radiation force exerted on the particles is stronger than the combined effect of fluid drag force and buoyancy and gravitational force, the particle is trapped within the acoustic standing wave field. This results in concentration, agglomeration and/or coalescence of the trapped particles. The strong lateral forces create rapid clustering of particles. Micron-sized particles, e.g., bacteria, mammalian cells, micro-algae, metal particles, yeast, fungi, lipids, oil droplets, red blood cells, white blood cells, platelets, etc., can thus be separated from the host fluid through enhanced gravitational separation. For the case of a suspension with several different particle sizes, it is possible by tuning of the system parameters to settle out the group of particles that are larger in size whereas the group of particles smaller in size can be kept in suspension. These two layers can then be harvested separately. A repeated process can then be used to fractionate groups of different sized particles according to size. In this regard, the multi-dimensional acoustic standing waves generated by each transducer can be of different frequencies.

One specific application for the acoustophoresis device is in the processing of bioreactor materials. It is important to be able to separate relatively larger cells and cell debris from the expressed materials that are in the host fluid. The expressed materials are composed of biomolecules such as recombinant proteins or monoclonal antibodies, and are the desired product to be recovered. Through the use of acoustophoresis, the separation of the cells and cell debris is very efficient and leads to very little loss of the expressed materials. This is an improvement over current filtration processes (depth filtration, tangential flow filtration, and the like), which show limited efficiencies at high cell densities, so that the loss of the expressed materials in the filter beds themselves can be up to 5% of the materials produced by the bioreactor. The use of mammalian cell cultures including Chinese hamster ovary (CHO), NS0 hybridoma cells, baby hamster kidney (BHK) cells, insect cells, and human cells (e.g. T-cells, B-cells, stem cells, red blood cells), and living/biological cells in general has proven to be a very efficacious way of producing/expressing the recombinant proteins and monoclonal antibodies required of today's pharmaceuticals. The filtration of the mammalian cells and the mammalian cell debris through acoustophoresis aids in greatly increasing the yield of the bioreactor. As desired, the acoustophoresis process may also be coupled with a standard filtration process upstream or downstream, such as depth filtration, tangential flow filtration (TFF), or other physical filtration processes.

Efficient separation has been demonstrated for CHO cells, T-cells, and yeast cells with separation efficiencies in excess of 90% and more for cell concentrations from as little as 50,000 cells per ml of fluid to 80 million cells per ml of fluid. The flow rates of the acoustic separation devices according to the current embodiments vary from 1 ml/min for smaller scale devices to in excess of 50 liter/hour for larger scale devices.

In this regard, the acoustic contrast factor is a function of the ratio of particle to fluid compressibility and particle to fluid density. Most cell types present a higher density and lower compressibility than the medium in which they are suspended, so that the acoustic contrast factor between the cells and the medium has a positive value. As a result, the axial acoustic radiation force (ARF) drives the cells, with a positive contrast factor, to the pressure nodal planes, whereas cells or other particles with a negative contrast factor are driven to the pressure anti-nodal planes. The radial or lateral component of the ARF is larger than the combined effect of fluid drag force and gravitational force. The radial or lateral component drives the cells/particles to specific locations (points) within these planes where they cluster, clump, agglomerate, or coalesce into larger groups, which will then continuously gravity separate from the fluid.

Desirably, the ultrasonic transducer(s) generate a three-dimensional or multi-dimensional acoustic standing wave in the fluid that exerts a lateral force on the suspended particles to accompany the axial force so as to increase the particle trapping and clumping capabilities of the standing wave. Typical results published in literature state that the lateral force is two orders of magnitude smaller than the axial force. In contrast, the technology disclosed in this application provides for a lateral force to be of the same order of magnitude as the axial force (i.e. a multi-dimensional acoustic standing wave). However, in certain embodiments described further herein, combinations of transducers that produce both multi-dimensional acoustic standing waves and planar standing waves are contemplated. For purposes of this disclosure, a standing wave where the lateral force is of the same order of magnitude as the axial force is considered a "multi-dimensional acoustic standing wave."

Figure 15:
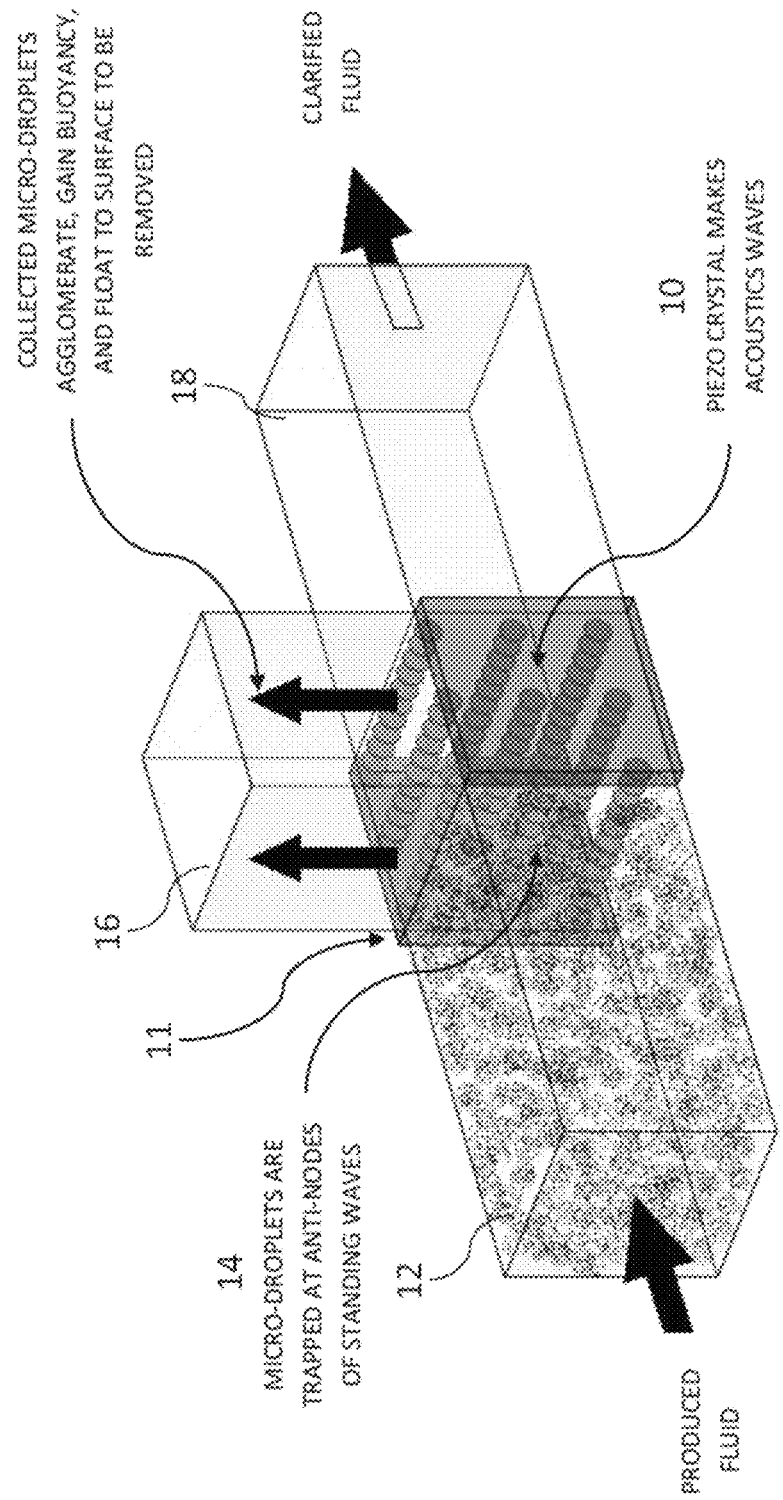
FIG. 15 is a diagram illustrating an acoustophoretic separation method according to the present disclosure for a second fluid or particle less dense than a host fluid.

A diagrammatic representation of an acoustic chamber for removing oil or other lighter-than-water material is shown in FIG. 15. Excitation frequencies typically in the range from hundreds of kHz to 10 s of MHz are applied by transducer 10. One or more standing waves are created between the transducer 10 and the reflector 11. Incoming host fluid containing a secondary phase enters at inlet 12. Microdroplets are trapped in standing waves at the pressure anti-nodes 14 where they agglomerate, aggregate, clump, or coalesce, and, in the case of buoyant material, float to the surface and are discharged via an effluent outlet 16 located above the flow path. Clarified fluid (e.g. water) is discharged at outlet 18. The acoustophoretic separation technology can accomplish multi-component particle separation without any fouling at a much reduced cost.

Figure 16:
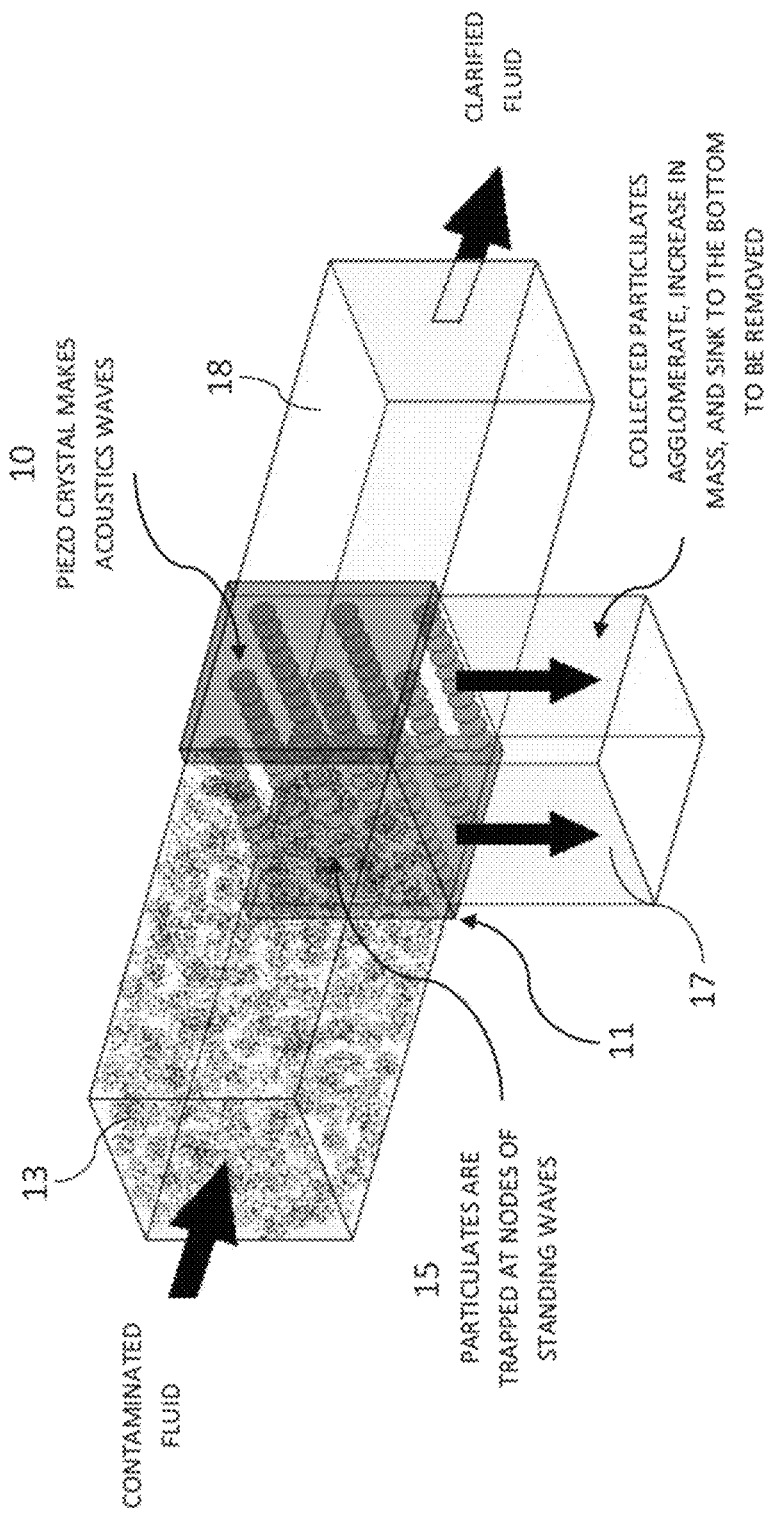
FIG. 16 is a diagram illustrating an acoustophoretic separation method according to the present disclosure for a second fluid or particle denser than a host fluid.

A diagrammatic representation of an acoustic chamber for removing contaminants or other heavier-than-water material is shown in FIG. 16. Excitation frequencies typically in the range from hundreds of kHz to 10 s of MHz are applied by transducer 10. Incoming contaminated fluid enters through inlet 13. Contaminants are trapped in standing waves at the pressure nodes 15 where they agglomerate, aggregate, clump, or coalesce, and, in the case of heavier material, sink to the bottom collector and are discharged via an effluent outlet 17 located below the flow path. Clarified fluid is discharged at outlet 18.

As previously explained, the ultrasonic transducer and reflector are located on opposite sides of the acoustic chamber. In this way, one or more acoustic standing waves are created between the ultrasonic transducer and reflector.

Prior to discussing further optimization of the systems, it is helpful to provide an explanation now of how multi-dimensional acoustic standing waves are generated. The multi-dimensional acoustic standing wave needed for particle collection is obtained by driving an ultrasonic transducer at a frequency that both generates the acoustic standing wave and excites a fundamental 3D vibration mode of the transducer piezoelectric element. The multi-dimensional acoustic standing wave may be generated by distinct modes of the piezoelectric element such as a 3×3 mode that would generate multidimensional acoustic standing waves. A multitude of multidimensional acoustic standing waves may also be generated by allowing the piezoelectric element to vibrate through many different mode shapes. Thus, the element would excite multiple modes such as a 0×0 mode (i.e. a piston mode) to a 1×1 (the fundamental mode), to 2×2, 1×3, 3×1, 3×3, and other higher order modes and then cycle back through the lower modes of the element (not necessarily in straight order). This switching or dithering of the piezoelectric element between modes allows for various multi-dimensional wave shapes, along with a single piston mode shape, to be generated over a designated time.

It is also possible to excite or choose a frequency of excitation that excites multiple modes at the same time, each mode with a varying degree of displacement amplitude. Through this combination of multiple modes excited at the same time with varying displacement amplitude, it is possible to generate a superposition of multi-dimensional standing waves desirable for trapping, clustering, and separation of a secondary fluid or particle from a host fluid.

The scattering of the acoustic field off the particles results in a three dimensional acoustic radiation force, which acts as a three-dimensional trapping field. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). When the acoustic radiation force exerted on the particles is stronger than the combined effect of fluid drag force and buoyancy and gravitational force, the particles are trapped within the acoustic standing wave field. This results in concentration, agglomeration and/or coalescence of the trapped particles. Relatively large solids of one material can thus be separated from smaller particles of a different material, the same material, and/or the host fluid through enhanced gravitational separation.

The multi-dimensional standing wave generates acoustic radiation forces in both the axial direction (i.e., in the direction of the standing wave, between the transducer and the reflector, perpendicular to the flow direction) and the lateral direction (i.e., in the flow direction). As the mixture flows through the acoustic chamber, particles in suspension experience a strong axial force component in the direction of the standing wave. Since this acoustic force is perpendicular to the flow direction and the drag force, it quickly moves the particles to pressure nodal planes or anti-nodal planes, depending on the contrast factor of the particle. The lateral acoustic radiation force then acts to move the concentrated particles towards the center of each planar node, resulting in agglomeration or clumping. The lateral acoustic radiation force component has to overcome fluid drag for such clumps of particles to continually grow and then drop out of the mixture due to gravity. Therefore, both the drop in drag per particle as the particle cluster increases in size, as well as the drop in acoustic radiation force per particle as the particle cluster grows in size, must be considered for the acoustic separator device to work effectively. In the present disclosure, the lateral force component and the axial force component of the multi-dimensional acoustic standing wave are of the same order of magnitude. In this regard, it is noted that in a multi-dimensional acoustic standing wave, the axial force is stronger than the lateral force, but the lateral force of a multi-dimensional acoustic standing wave is much higher than the lateral force of a planar standing wave, usually by two orders of magnitude or more.

Some further explanation of the ultrasonic transducers used in the devices, systems, and methods of the present disclosure may be helpful as well. In this regard, the transducers use a piezoelectric element, usually made of PZT-8 (lead zirconate titanate). Such elements may have a 1 inch by 1 inch square shape with a thickness of 1 mm (nominal 2 MHz resonance frequency), and may also be of a larger size, such as a 1 inch by 3 inch shape with a 1 mm thickness, or smaller such as 0.5 inch by 0.5 inch. The thickness controls the resonance frequency, as the resonance frequency is inversely proportional to thickness. Each ultrasonic transducer module can have only one piezoelectric element, or can have multiple elements that each act as a separate ultrasonic transducer and are either controlled by one or multiple amplifiers. The piezoelectric element(s) can be crystalline, semi-crystalline, or non-crystalline. The transducer(s) is/are used to create a pressure field that generates forces of the same order of magnitude both orthogonal to the standing wave direction (lateral) and in the standing wave direction (axial).

Figure 17:
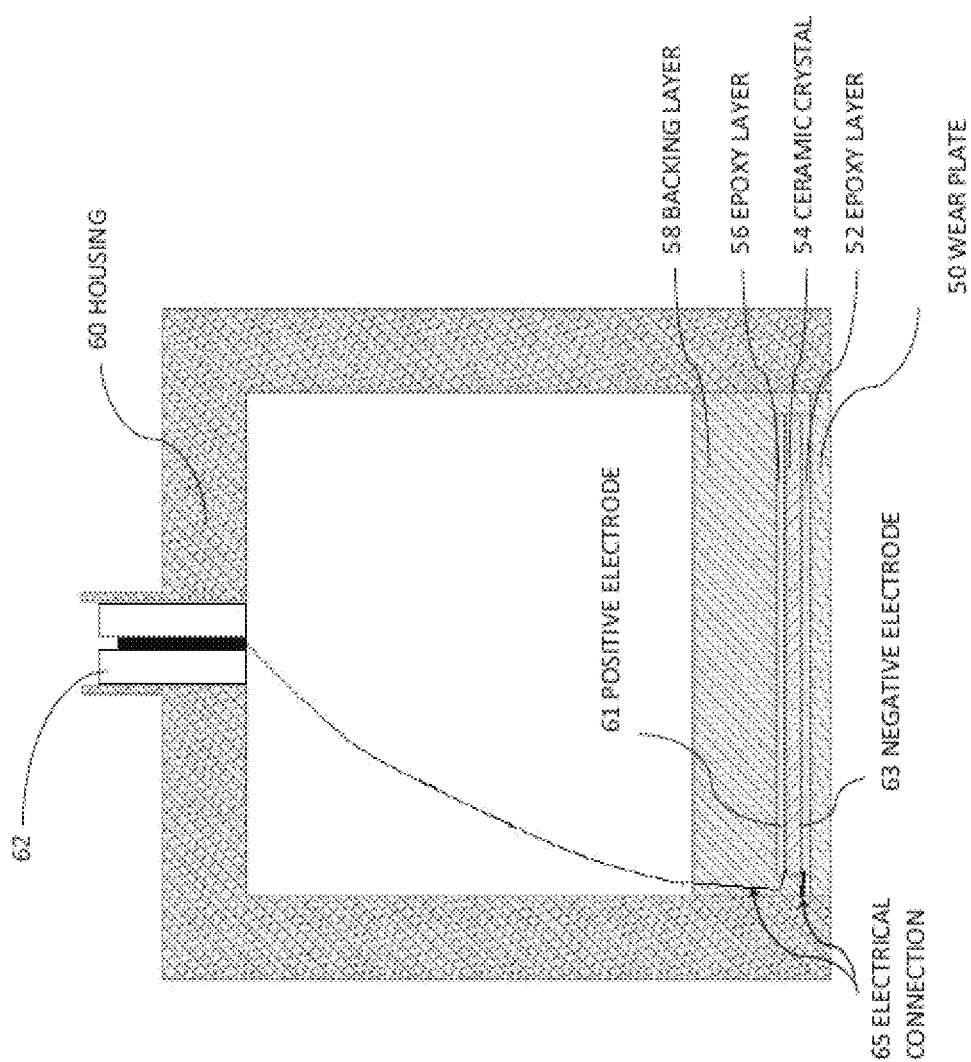
FIG. 17 is a cross-sectional diagram of a conventional ultrasonic transducer.

FIG. 17 is a cross-sectional diagram of a conventional ultrasonic transducer. This transducer has a wear plate 50 at a bottom end, epoxy layer 52, piezoelectric element 54 (e.g. a ceramic crystal made of, e.g. PZT), an epoxy layer 56, and a backing layer 58. On either side of the piezoelectric element, there is an electrode: a positive electrode 61 and a negative electrode 63. The epoxy layer 56 attaches backing layer 58 to the piezoelectric element 54. The entire assembly is contained in a housing 60 which may be made out of, for example, aluminum. An electrical adapter 62 provides connection for wires to pass through the housing and connect to leads (not shown) which attach to the piezoelectric element 54. Typically, backing layers are designed to add damping and to create a broadband transducer with uniform displacement across a wide range of frequency and are designed to suppress excitation at particular vibrational eigen-modes. Wear plates are usually designed as impedance transformers to better match the characteristic impedance of the medium into which the transducer radiates.

Figure 18:
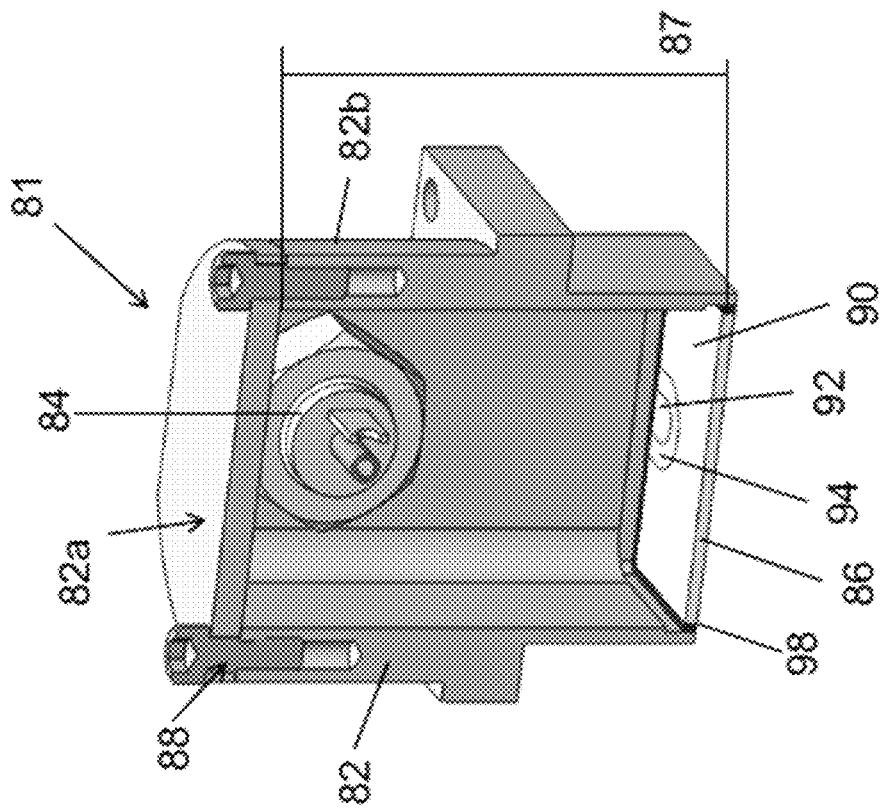
FIG. 18 is a cross-sectional diagram of an ultrasonic transducer according to the present disclosure. An air gap is present within the transducer, and no backing layer or wear plate is present.

FIG. 18 is a cross-sectional view of an ultrasonic transducer 81 of the present disclosure. Transducer 81 is shaped as a disc or a plate, and has an aluminum housing 82. The piezoelectric element can be, e.g., a mass of perovskite ceramic crystals, each consisting of a small, tetravalent metal ion, usually titanium or zirconium, in a lattice of larger, divalent metal ions, usually lead or barium, and O2− ions. As an example, in the embodiment shown in FIG. 18, a PZT (lead zirconate titanate) crystal 86 defines the bottom end of the transducer, and is exposed from the exterior of the housing. The crystal is supported on its perimeter by a small elastic layer 98, e.g. silicone or similar material, located between the crystal and the housing. Put another way, no wear layer is present. In particular embodiments, the crystal is an irregular polygon, and in further embodiments is an asymmetrical irregular polygon.

Figure 19:
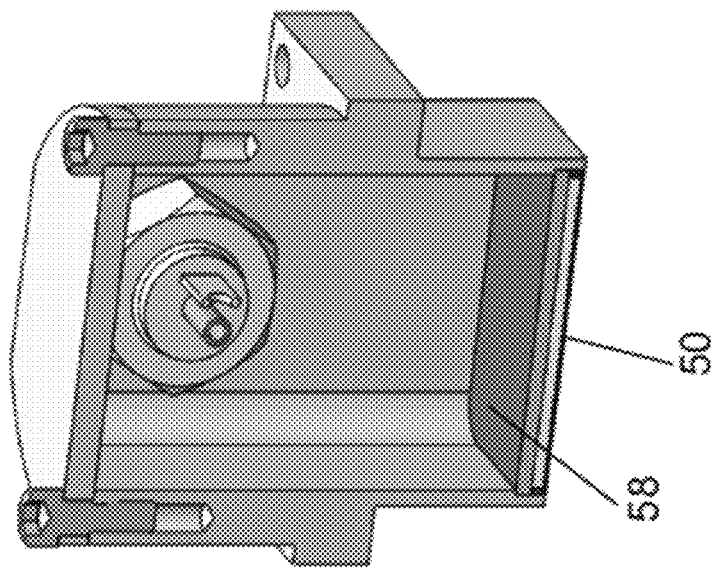
FIG. 19 is a cross-sectional diagram of an ultrasonic transducer according to the present disclosure. An air gap is present within the transducer, and a backing layer and wear plate are present.

Screws 88 attach an aluminum top plate 82a of the housing to the body 82b of the housing via threads. The top plate includes a connector 84 for powering the transducer. The top surface of the PZT crystal 86 is connected to a positive electrode 90 and a negative electrode 92, which are separated by an insulating material 94. The electrodes can be made from any conductive material, such as silver or nickel. Electrical power is provided to the PZT crystal 86 through the electrodes on the crystal. Note that the crystal 86 has no backing layer or epoxy layer. Put another way, there is an air gap 87 in the transducer between aluminum top plate 82a and the crystal 86 (i.e. the air gap is completely empty). A minimal backing 58 and/or wear plate 50 may be provided in some embodiments, as seen in FIG. 19.

The transducer design can affect performance of the system. A typical transducer is a layered structure with the piezoelectric element bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the piezoelectric element to vibrate in one of its eigenmodes (i.e. near eigenfrequency) with a high Q-factor. The vibrating piezoelectric element, such as, e.g., a ceramic crystal/disk, is directly exposed to the fluid flowing through the acoustic chamber.

Removing the backing (e.g. making the piezoelectric element air backed) also permits the element to vibrate at higher order modes of vibration with little damping (e.g. higher order modal displacement). In a transducer having a piezoelectric element with a backing, the element vibrates with a more uniform displacement, like a piston. Removing the backing allows the element to vibrate in a non-uniform displacement mode. The higher order the mode shape of the piezoelectric element, the more nodal lines the element has. The higher order modal displacement of the element creates more trapping lines, although the correlation of trapping line to node is not necessarily one to one, and driving the element at a higher frequency will not necessarily produce more trapping lines.

In some embodiments, the piezoelectric element may have a backing that minimally affects the Q-factor of the crystal (e.g. less than 5%). The backing may be made of a substantially acoustically transparent material such as balsa wood, foam, or cork which allows the element to vibrate in a higher order mode shape and maintains a high Q-factor while still providing some mechanical support for the element. The backing layer may be a solid, or may be a lattice having holes through the layer, such that the lattice follows the nodes of the vibrating element in a particular higher order vibration mode, providing support at node locations while allowing the rest of the element to vibrate freely. The goal of the lattice work or acoustically transparent material is to provide support without lowering the Q-factor of the piezoelectric element or interfering with the excitation of a particular mode shape.

Placing the piezoelectric element in direct contact with the fluid also contributes to the high Q-factor by avoiding the dampening and energy absorption effects of the epoxy layer and the wear plate. Other embodiments may have wear plates or a wear surface to prevent the PZT, which contains lead, contacting the host fluid. This may be desirable in, for example, biological applications such as separating blood. Such applications might use a wear layer such as chrome, electrolytic nickel, or electroless nickel. Chemical vapor deposition could also be used to apply a layer of poly(p-xylylene) (e.g. Parylene) or other polymers or polymer films. Organic and biocompatible coatings such as silicone or polyurethane are also usable as a wear surface.

The lateral force of the total acoustic radiation force (ARF) generated by the ultrasonic transducers of the present disclosure is significant and is sufficient to overcome the fluid drag force at high linear velocities up to 1 cm/s and beyond. For example, linear velocities through the devices of the present disclosure can be a minimum of 4 cm/min for separation of cells/particles, and can be as high as 1 cm/sec for separation of oil/water phases.

The lateral force of the acoustic radiation force generated by the transducer can be increased by driving the transducer in higher order mode shapes, as opposed to a form of vibration where the piezoelectric element effectively moves as a piston having a uniform displacement. The acoustic pressure is proportional to the driving voltage of the transducer. The electrical power is proportional to the square of the voltage. The voltage signal can have a sinusoidal, triangular, pulsed, or similar waveform and can have a frequency of from about 100 kHz to about 20 MHz. The transducer is typically a thin piezoelectric plate, with electric field in the z-axis and primary displacement in the z-axis. The transducer is typically coupled on one side by air (i.e., the air gap within the transducer) and on the other side by the fluid mixture of the cell culture media. The types of waves generated in the plate are known as composite waves. A subset of composite waves in the piezoelectric plate is similar to leaky symmetric (also referred to as compressional or extensional) Lamb waves. The piezoelectric nature of the plate typically results in the excitation of symmetric Lamb waves. The waves are leaky because they radiate into the water layer, which result in the generation of the acoustic standing waves in the water layer. Lamb waves exist in thin plates of infinite extent with stress free conditions on its surfaces. Because the transducers of this embodiment are finite in nature, the actual modal displacements are more complicated.

Generally, the transducers of the present disclosure are used to create a pressure field that generates acoustic radiation forces of the same order of magnitude both orthogonal to the standing wave direction and in the standing wave direction. When the forces are roughly the same order of magnitude, particles of size 0.1 microns to 300 microns will be moved more effectively towards "trapping lines," so that the particles will not pass through the pressure field. Instead, the particles will remain within the acoustic chamber, from which they can advantageously be collected via specified outlets of the acoustophoretic device or otherwise recycled back to an associated bioreactor.

The acoustophoretic devices and methods described herein are useful for separating a second fluid or particulate from a host fluid. In this regard, the devices and methods of the present disclosure utilize higher order modal displacement of a piezoelectric material having a non-planar face, such that the piezoelectric material may be perturbed by a single excitation, yet still generate multi-dimensional acoustic standing waves.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. An acoustophoretic device, comprising:
an acoustic chamber;
at least one ultrasonic transducer coupled to the acoustic chamber and including a piezoelectric material, for launching an acoustic wave in the acoustic chamber; and
a reflector that includes a non-planar face and that is located across the acoustic chamber from the at least one ultrasonic transducer, the non-planar face being faceted.

2. The acoustophoretic device of claim 1, wherein the reflector includes a planar face opposite the non-planar face and is composed of piezoelectric material that is poled in a direction substantially perpendicular to the planar face of the reflector.

3. The acoustophoretic device of claim 1, wherein the non-planar face of the reflector includes a shape that is defined by a step function or a smooth function.

4. The acoustophoretic device of claim 1, wherein the piezoelectric material has a non-planar face.

5. The acoustophoretic device of claim 4, wherein the non-planar face of the piezoelectric material includes a shape that is defined by a step function or a smooth function.

6. The acoustophoretic device of claim 1, wherein the non-planar face of the reflector includes a plurality of adjoining portions, each of which are located at respective distances from a respective closest portion of the piezoelectric material, the respective distances being different.

7. The acoustophoretic device of claim 6, wherein the respective distance of each adjoining portion from the respective closest portion of the piezoelectric material defines a resonance for an acoustic wave to be established.

8. The acoustophoretic device of claim 7, wherein the collective respective distances define a plurality of distinct resonances that match resonances for the acoustic wave to be established in the acoustic chamber as resonance conditions in the acoustic chamber vary.

9. The acoustophoretic device of claim 1, wherein the acoustic wave is configured to collect cells at cell concentrations of greater than or equal to 50,000 cells per milliliter of fluid.

10. A method for separating a second fluid or a particulate from a host fluid, comprising:
   flowing a mixture of the host fluid and the second fluid or particulate through an acoustophoretic device, the acoustophoretic device comprising:
   an acoustic chamber;
   at least one ultrasonic transducer coupled to the acoustic chamber and including a piezoelectric material, for launching an acoustic wave in the acoustic chamber; and
   a reflector that includes a non-planar face and that is located across the acoustic chamber from the at least one ultrasonic transducer, the non-planar face being faceted;
   exciting the at least one ultrasonic transducer to launch the acoustic wave in the acoustic chamber;
   reflecting the acoustic wave with the reflector to generate an acoustic field in the acoustic chamber, and
   separating the second fluid or particulate from the host fluid using the acoustic field as the mixture flows through the acoustic field in the acoustophoretic device.

11. The method of claim 10, wherein the piezoelectric material includes a non-planar face.

12. The method of claim 11, wherein the non-planar face of the piezoelectric material includes a shape that is defined by a step function or a smooth function.

13. The method of claim 10, wherein the non-planar face of the reflector includes a shape that is defined by a step function or a smooth function.

14. The method of claim 10, wherein the piezoelectric material has a non-symmetrical shape.

15. The method of claim 10, wherein the reflector has a non-symmetrical shape.

16. The method of claim 10, wherein the non-planar face of the reflector includes a plurality of adjoining portions, each of which are located at respective distances from a respective closest portion of the piezoelectric material, the respective distances being different.

17. The method of claim 16, further comprising changing a resonance of the acoustic standing wave by changing a distance between the at least one transducer and the reflector that is occupied by the acoustic standing wave.

18. The method of claim 10, wherein the mixture is continuously flowed through the acoustic chamber at a flow rate of from about 1 milliliter per minute to about 50 liters per hour.

19. The method of claim 10, wherein the acoustic standing wave is a multi-dimensional acoustic standing wave that includes an axial force component and a lateral force component which are of the same order of magnitude.

20. The method of claim 10, further comprising changing the resonance of the acoustic standing wave according to changing conditions in the acoustic chamber.

21. The method of claim 10, wherein the second fluid or particulate includes at least one cell selected from the group consisting of CHO cells, T-cells, and yeast cells.

22. An acoustophoretic device, comprising:
   an acoustic chamber;
   at least one ultrasonic transducer coupled to the acoustic chamber that includes a piezoelectric material that is configured to be excited to generate an acoustic wave in the acoustic chamber; and
   a reflector located across the acoustic chamber from the at least one ultrasonic transducer, the reflector including a faceted surface that faces the at least one ultrasonic transducer.

23. The acoustophoretic device of claim 1, wherein the faceted, non-planar face of the reflector includes a plurality of facet clusters.

24. The acoustophoretic device of claim 1, wherein the faceted, non-planar face of the reflector includes a plurality of wells.

25. The acoustophoretic device of claim 1, wherein the non-planar face of the reflector is arranged in regular stepped facets.

* * * * *